(12) United States Patent
Plettenburg et al.

(10) Patent No.: US 8,461,144 B2
(45) Date of Patent: Jun. 11, 2013

(54) SUBSTITUTED ISOQUINOLINE AND ISOQUINOLINONE DERIVATIVES

(75) Inventors: Oliver Plettenburg, Kelkheim (DE); Armin Hofmeister, Dexheim (DE); Joachim Brendel, Bad Vibel (DE); Matthias Lohn, Liederbach (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/586,468

(22) Filed: Aug. 15, 2012

(65) Prior Publication Data

US 2012/0316152 A1    Dec. 13, 2012

Related U.S. Application Data

(60) Division of application No. 12/487,403, filed on Jun. 18, 2009, now Pat. No. 8,278,294, which is a continuation of application No. PCT/EP2007/011163, filed on Dec. 19, 2007.

(30) Foreign Application Priority Data

Dec. 27, 2006    (EP) .................................. 06026898

(51) Int. Cl.
    *A61K 31/397*    (2006.01)
(52) U.S. Cl.
    USPC .................................................. 514/210.21
(58) Field of Classification Search
    USPC .................................................. 514/210.21
    See application file for complete search history.

(56) References Cited

U.S. PATENT DOCUMENTS

| | | | |
|---|---|---|---|
| 5,480,883 A | 1/1996 | Spada et al. | |
| 6,903,107 B1 | 6/2005 | Timmers et al. | |
| 7,217,722 B2 | 5/2007 | Takami et al. | |
| 7,618,985 B2 | 11/2009 | Ray et al. | |
| 2003/0220368 A1 | 11/2003 | Ozaki et al. | |
| 2004/0138286 A1 | 7/2004 | Imazaki et al. | |
| 2006/0079556 A1 | 4/2006 | Sher et al. | |
| 2007/0060595 A1 | 3/2007 | Yoshizawa et al. | |
| 2007/0135479 A1 | 6/2007 | Ray | |
| 2008/0045566 A1 | 2/2008 | Ray et al. | |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 | 4/1998 |
| WO | 9202476 | 2/1992 |
| WO | 9706802 | 2/1997 |
| WO | 9723214 | 7/1997 |
| WO | 9806433 | 2/1998 |
| WO | 9911642 | 3/1999 |
| WO | 0024718 | 5/2000 |
| WO | 0073299 | 12/2000 |
| WO | 0139726 | 6/2001 |
| WO | 0153288 | 7/2001 |
| WO | 0156988 | 8/2001 |
| WO | 0164238 | 9/2001 |
| WO | 0164656 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | 03053330 | 7/2003 |
| WO | 2004106325 | 12/2004 |
| WO | 2004113297 | 12/2004 |
| WO | 2005035933 | 2/2005 |
| WO | 2005030130 | 4/2005 |
| WO | 2005030791 | 4/2005 |
| WO | 2005035516 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | 2007000240 | 1/2007 |
| WO | 2007012421 | 2/2007 |
| WO | 2007012422 A1 | 2/2007 |
| WO | 2007039563 A1 | 4/2007 |

(Continued)

OTHER PUBLICATIONS

Masumoto, A., et al., "Suppression of Coronary Artery Spasm by the Rho-Kinase Inhibitor Fasudil in Patients With Vasospastic Angina", Circulation, (2002), vol. 105, pp. 1545-1547.

Nakahara, T., et al., "Y-27632 Potentiates Relaxant Effects of B2-Adrenoceptor Agonists in Bovine Tracheal Smooth Muscle", European Journal of Pharmacology, vol. 389, (2000), pp. 103-106.

(Continued)

*Primary Examiner* — Brandon Fetterolf
*Assistant Examiner* — Christopher R Stone
(74) *Attorney, Agent, or Firm* — Thomas Loeschner; Scully, Scott, Murphy & Presser, P.C.

(57)    ABSTRACT

A method for the treatment or prevention in a mammal of a disease associated with Rho-kinase and/or Rho-kinase mediated phosphorylation of myosin light chain phosphatase comprising administering to the mammal in need thereof at least one compound of the formula (I).

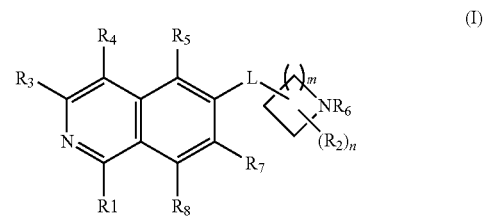

20 Claims, No Drawings

FOREIGN PATENT DOCUMENTS

| | | |
|---|---|---|
| WO | 2007065916 | 6/2007 |
| WO | 2008020081 | 2/2008 |
| WO | 2008020081 A1 | 2/2008 |
| WO | 2008077555 A2 | 7/2008 |
| WO | 2008077556 A1 | 7/2008 |

OTHER PUBLICATIONS

Negoro, N., et al., "The Kinase Inhibitor Fasudil (HA-1077) Reduces Intimal Hyperplasia through Inhibiting Migration and Enhancing Cell Loss of Vascular Smooth Muscle Cells", Biochemical Research Communications, vol. 262, pp. 211-215, (1999).

Noma, K., et al., "Physiological Role of ROCKS in the Cardiovascular System", Am. J. Physiol, Cell Physiol, vol. 290 pp. C661-C668, (2006).

Pacaud, P., et al., "Rho Proteins and Vascular Diseases", Archives Des Maladies Du CCeur Et Des Valsseaux, vol. 98, pp. 249-254, (2005).

Pommereau, A., et al., "Two Simple and Generic Antibody-Independent Kinase Assays: Comparison of a Bioluminescent and a Microfluidic Assay Format", J. Biomol. Screen, (2004), vol. 9, pp. 409-416.

Retzer, M., et al., "Lysophosphatidic Acid-Induced Platelet Shape Change Proceeds Via Rho/Rho Kinase-Medicated Myosin Light-Chain and Moesin Phosphorylation", Cellular Signaling, vol. 12, pp. 645-648, (2000).

Retzer, M., et al., "Mildly Oxidized Low Density Lipoprotein Induces Platelet Shape Change Via Rho-Kinase-Dependent Phosphorylation of Myosin Light Chain and Moesin", FEBS Letters, vol. 486, pp. 70-74, (2000).

Sandu, O. A., et al., "Diabetes in the Goto-Kakizaki Rat is Accompanied by Impaired Insulin-Mediated Myosin-Bound Phosphatase Activation and Vascular Smooth Muscle Cell Relaxation", Diabetes, vol. 49, (2000), pp. 2178-2189.

Sato, M., et al., "Involvement of Rho-Kinase-Mediated Phosphorylation of Myosin Light Chain in Enhancement of Cerebral Vasospasm", Circulation Research, (2000), vol. 87, pp. 195-200.

Satoh, S. I, "Pharmacological Profile of Hydroxy Fasudil as a Selective Rho Kinase Inhitor on Ischemic Brain Damage", Life Sciences, vol. 69, (2001), pp. 1441-1453.

Seasholtz, T. M., et al., "Rho and Rho Kinase Mediate Thrombin-Stimulated Smooth Muscle Cell DNA Synthesis and Migration", Circulation Research, (1999), vol. 84, pp. 1186-1193.

Setoguchi, H., et al., "Leuotriene C4 Enhances the Contraction of Porcine Tracheal Smooth Muscle Through the Activation of Y-27632, a Rho Kinase Inhibitor, Sensitive Pathway", British Journal of Pharmacology, (2001), vol. 132, pp. 111-118.

Shimokawa, H., et al., "Anti-Anginal Effect of Fasudil, a Rho-Kinase Inhibitor, in Patients With Stable Effort Angina: A Multicenter Study", Journal of Cardiovascular Pharmacology, (2002), vol. 40, pp. 751-761.

Somlyo, A. V., et al., "Rho-Kinase Inhibitor Retards Migration and In-Vivo Dissemination of Human Prostate Cancer Cells", Biochemical and Biophysical Research Communications, vol. 269, pp. 652-659, (2000).

Steioff, K., et al., "Long Term Rho-Kinase Inhibition Ameliorates Endothelial Dysfunction in LDL Receptor Deficient Mice", European Journal of Pharmacology, vol. 512, (2005), pp. 247-249.

Tatsumi, S., et al., "Involvement of Rho-Kinase in Inflammatory and Neuropathic Pain Through Phosphorylation of Myristoylated Alainine-Rich C-Kinase Substrate (MARCKS)", Neuroscience, vol. 131, pp. 491-498, (2005).

Totsukawa, G., et al., "Distinct Roles of ROCK (Rho-Kinase) and MLCK in Spatial Regulation of MLC Phosphorylation for Assembly of Stress Fibers and Focal Adhesions in 3T3 Fibroblasts", The Journal of Cell Biology, vol. 150, No. 4, pp. 797-806, (2000).

Uchida, S., et al., "The Suppression of Small GTPase Eho Signal Transduction Pathway Inhibits Angiogenesis in Vitro and In Vivo", Biochemical and Biophysical Research Communications, vol. 269, pp. 633-640, (2000).

Uehata, M., et al., "Calcium Sensitization of Smooth Muscle Mediated by a Rho-Associated Protein Kinase in Hypertension", Nature, vol. 389, pp. 990-994, (1997.

Vicente-Manzanares, M., et al., "A Role for the Rho-p160 Rho Coiled-Coil Kinase Axis in the Chemokine Stromal Cell-Derived Factor-1a-Induced Lymphocyte Actomyosin and Microtubular Organization and Chemotaxis", The Journal of Immunology, (2002), vol. 168, pp. 400-410.

Vicente-Manzanares, M., et al., "The RhoA Effector MDia is Induced During T Cell Activation and Regulates Actin Polymerization and Cell Migration in T Lymphocytes", The Journal of Immunology, (2003), vol. 171, pp. 1023-1034.

Wakino, S., et al., "Rho/Rho Kinase as a Potential Target for the Treatment of Renal Disease", Drug News Perspective, (2005), vol. 18, pp. 639-643.

Yamakawa, T., et al., "Involvement of Rho-Kinase in Angiotension II-Induced Hypertrophy of Rat Vascular Smooth Muscle Cells", Hypertension, (2000), vol. 35, pp. 313-318.

Yamamoto, Y., et al., "The Protein Kinase Inhibitor Fasudil Protects Against Ischemic Myocardial Injury Induced by Endothelin-1 in the Rabbit", Journal of Cardiovascular Pharmacology, vol. 35, pp. 203-211, (2000).

Yoshida, Y., et al., "Studies on Anti-Helicobacter pylori Agents, Part 1: Benzyloxyisoquinoline Derivatives", Bloorg. & Med. Chem., vol. 7, (1999), pp. 2647-2666.

Yoshi, A., et al., "Relaxation of Contracted Rabbit Tracheal and Human Bronchial Smooth Muscle by Y-27632 Through Inhibition of Ca2+ Sensitization", Am. J. Resp. Cell Mol. Biol., vol. 20, pp. 1190-1200, (1999).

Zhou, Y., et al., "Nonsteroidal Anti-Inflammatory Drugs Can Lower Amyloidogenic AB42 by Inhibiting Rho", Science, vol. 302, pp. 1215-1217, (2003).

Alvarez, M. et al., "Product Class 5: Isoquinolines", Science of Synthesis (2005) pp. 661-838, vol. 15.

Alvarez, M. et al., "Product Class 6: Isoquinolines" Science of Synthesis (2005) pp. 839-890, vol. 15.

Remington's Pharmaceutical Sciences 17th Edition (1985), p. 1418.

Forzato, C. et al., "Baker's yeast reduction of 4-hetero-2-(2-nitroethyl)cyclohexanones" Tetrahedron: Asymmetry (1997) pp. 1811-1820, vol. 8.

U.S. Appl. No. 12/970,376, filed Dec. 16, 2010, Inventor: Plettenburg, et al, entitled: "6-Substituted Isoquinolines and Isoquinolinones".

U.S. Appl. No. 13/000,754, filed Apr. 20, 2011, Inventor: Plettenburg et al., entitled: "Substituted Isoquinolines and Isoquinolinones as Rho Kinase Inhibitors".

U.S. Appl. No. 13/000,202, filed Dec. 20, 2010, Inventor: Plettenburg et al., entitled: "Bi- and Polycyclic Substituted Isoquinoline and Isoquinolinone Derivatives".

Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.

Curran, T.T. et al., "The Preparation of Optically Active 2-Cyclopenten-1,4-Diol Derivatives from Furfurl Alcohol" Tetrahedron, pp. 1983-2004, vol. 53(6).

Tamura, M. et al., "Development of Specific Rho-Kinase Inhibitors and Their Clinical Application" Biochimicia et Blophysica Acta (2005) pp. 245-252, vol. 1754.

Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.

Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.

Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.

Caron, S. et al., "The Synthesis of a Selective PDE4/TNFα Inhibitor" Organic Process Research and Development (2001) pp. 587-592, vol. 5.

Takami, A. et al., "Design and Synthesis of Rho Kinase Inhibitors (I)" Bioorganic & Medicinal Chemistry (2004) pp. 2115-2137, vol. 12.

Iwakubo, M. et al., "Design and Synthesis of Rho Kinase Inhibitors (III)" Bioorganic & Medicinal Chemistry (2007) pp. 1022-1033, vol. 15.
Iwakubo, M. et al., "Design and Synthesis of Rho Kinase Inhibitors (II)" Bioorganic & Medicinal Chemistry (2007) pp. 350-364, vol. 15.
U.S. Appl. No. 11/961,193, filed Dec. 20, 2007, Inventor: Plettenburg et al., entitled: "Isoquinoline Derivatives".
U.S. Appl. No. 12/019,866, filed Jan. 25, 2008, Inventor: Plettenburg et al., entitled: "Piperidinyl-Substituted Isoquinolone Derivatives".
U.S. Appl. No. 12/019,799, filed Jan. 25, 2008, Inventor: Plettenburg et al., entitled: "Cyclohexylamin Isoquinolone Derivatives".
U.S. Appl. No. 12/487,479, filed Jun. 18, 2009, Inventor: Plettenburg et al., entitled: "Cycloalkylamine Substituted Isoquinolone Derivatives".
U.S. Appl. No. 12/487,455, filed Jun. 18, 2009, Inventor: Plettenburg et al., entitled: "Substituted Isoquinoline and Isoquinolinone Derivatives".
U.S. Appl. No. 12/487,525, filed Jun. 18, 2009, Inventor: Plettenburg et al., entitled: "Cycloalkylamine Substituted Isoquinolone and Isoquinolinone Derivatives".
U.S. Appl. No. 12/487,386, filed Jun. 18, 2009, Inventor: Plettenburg et al., entitled: "Cycloalkylamine Substituted Isoquinoline Derivatives".
U.S. Appl. No. 12/487,409, filed Jun. 18, 2009, Inventor: Plettenburg et al., entitled: "New Substituted Isoquinoline and Isoquinolinone Derivatives".
U.S. Appl. No. 12/487,503, filed Jun. 18, 2009, Inventor: Plettenburg et al., entitled: "Cycloalkylamine Substituted Isoquinoline and Isoquinolinone Derivatives".
Al, S., et al., "Rho-Rho Kinase is Involved in Smooth Muscle Cell Migration Through Myosin Light Chain Phosphorylation-Dependent and Independent Pathways", Atherosclerosis, vol. 155, pp. 321-327, (2001).
Amano, M. et al., "Formation of Actin Stress Fibers and Focal Adhesions Enhanced by Rho-Kinase", Science, vol. 275, pp. 1308-1311, (1997).
Bauer, M. et al., "Dichotomous Regulation of Myosin Phosphorylation and Shape Change by Rho-Kinase and Calcium in Intact Human Platelets", Blood, vol. 94, No. 5, pp. 1665-1672, (1999).
Chellaiah, M. et al., "Rho-Dependent Rho Kinase Activation Increases CD44 Surface Expression and Bone Resorption in Osteoclasts", The Journal of Biological Chemistry, vol. 278, No. 31, pp. 29086-29097, (2003).
Chitaley, K. et al., "Antagonism of Rho-Kinase Stimulates Rat Penile Erection Via a Nitric Oxide-Independent Pathway", Nature Medicine, vol. 7, No. 1, pp. 119-122, (2001).
Demiryurek, S., et al., "Effects of Fasudil, a Rho-Kinase Inhibitor, On Myocardial Preconditioning in Anesthetized Rats", European Journal of Pharmacology, vol. 527, pp. 129-140, (2005).
Fukumoto, Y., et al., "Acute Vasodilator Effects of a Rho-Kinase Inhibitor, Fasudil, in Patients With Severe Pulmonary Hypertension", Heart, (2005), vol. 91, pp. 391-392.
Furukawa, N., et al., "Role of Rho-Kinase in Regulation of Insulin Action and Glucose Homeostasis", Cell Metabolism, vol. 2, pp. 119-129, (2005).
Gingras, D., et al., "Tyrosine Phosphorylation of thee Vascular Endothelial-Growth-Factor Receptor-2(VEGFR-2) is Modulated by Rho Proteins", Biochem. J., (2000), vol. 348, pp. 273-280.
Gokina, N. I., et al., "Effects of Rho Kinase Inhibition on Cerebral Artery Myogenic Tone and Reactivity", J. Appl. Physiol., vol. 98, pp. 1940-1948, (2005).
Hara, M., et al., "Protein Kinase Inhibition by Fasudi Hydrochloride Promotes Neurological Recovery After Spinal Cord Injury in Rats", J Neurosurg. (Spine 1), vol. 93, pp. 94-101, (2000).
Hattori, T., et al., "Long-Term Inhibition of Rho-Kinase Suppresses Left Ventricular Remodeling After Myocardial Infarction in Mice", Circulation, (2004), vol. 109, pp. 2234-2239.
Okada, H., et al., "Synthesis and Antitumor Activities of Prodrugs of Benzoylphenyiureas", Chem. Pharm. Bull, (1994), pp. 57-61, vol. 42, No. 1.
Hitomi, A., et al., "Hemorheological Abnormalities in Experimental Cerebral Ischemia and Effects of Protein Kinase Inhibitor on Blood Fluidity", Life Science, vol. 67, (2000), pp. 1929-1939.
Honjo, M., et al., "Effects of Rho-Associated Protein Kinase Inhibitors Y-27632 on Intraocular Pressure and Outflow Facitliy", Investigative Ophthalmology & Visual Science, (2001), vol. 42, No. 1, pp. 137-144.
Inoue, M., et al., "Initiation of Neuropathic Pain Requires Lysophospatidic Acid Receptor Signaling", Nature Medicine, vol. 10, No. 7, pp. 712-718, (2004).
Itoh, et al., "An Essential Part for Rho-Associated Kinase in the Transcellular Invasion of Tumor Cells", Nature Medicine, vol. 5, No. 2, pp. 221-225, (1999).
Kawaguchi, A., et al., "The Effect of a Rho Kinase Inhibitor Y-27632 on Superoxide Production, Aggregation and Adhesion in Human Polymorphonuclear Leukocytes", European Journal of Pharmacology, vol. 403, (2000), pp. 203-208.
Kim, I, et al., "Think and Thick Filament Regulation of Contractility in Experimental Cerebral Vasospasm", Neurosurgery, vol. 46, No. 2, (2000), pp. 440-447.
Kimura, K., et al., "Regulation of the Association of Adducin With Actin Filaments by Rho-Associated Kinase (Rho-Kinase) and Myosin Phosphatase", The Journal of Biological Chemistry, vol. 273, No. 10, pp. 5542-5546.
Kishi, T., et al., "Rho-Kinase Inhibitor Improves Increased Vascular Resistance and Impaired Vasodilation of the Forearm in Patients with Heart Failure", Circulation, (2005), vol. 111, pp. 2741-2747.
Klages, B., et al., "Activation of G12/G13 Results in Shape Change and Rho/Rho-Kinase-Medicated Myosin Light Chain Phosphorylation in Mouse Platelets", The Journal of Cell Biology, vol. 144, No. 4, (1999), pp. 745-754.
Lin, T., et al., "Rho-ROCK-LIMK-Cofilin Pathway Regulates Shear Stress Activation of Sterol Regulatory Element Binding Proteins", Circulation Research, (2003), vol. 92, pp. 1296-1304.
Maruoka, S., et al., "Elastase Anti-Elastase Imbalance in the Pathogenesis of COPD", Nippon Rinsho, (1999), vol. 57, pp. 1982-1987.

SUBSTITUTED ISOQUINOLINE AND ISOQUINOLINONE DERIVATIVES

CROSS-REFERENCE

This application is a Divisional of U.S. patent application Ser. No. 12/487,403 filed Jun. 18, 2009, which is a Continuation of International Application No. PCT/EP2007/011163, filed Dec. 19, 2007, which claims priority to EP 06026898.4, filed Dec. 27, 2006, all of which are incorporated herein by reference in their entirety.

FIELD OF THE INVENTION

The present invention relates to novel isoquinoline and isoquinolinone derivatives as described in the claims, their preparation and their use in the treatment and/or prevention of diseases related to the inhibition of Rho-kinase and/or of Rho-kinase mediated phosphorylation of myosin light chain phosphatase.

BACKGROUND OF THE INVENTION

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J. Pharmacol. 2001, 132, 111-8; Nakahara, et al. Eur J 2000, 389,103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraoccular pressure (Honjo et al. Invest. Ophthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-43), myocardial infarction (Demiryurek et al. Eur J. Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, artherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Nara, et al. J Neurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J. Pharmacol. 2000, 403, 203-8; Sanchez-Madrid, et al. J. Immunol. 2003, 171, 1023-34, Sanchez-Madrid, et al. J. Immunol. 2002, 168, 400-10), and bone resorption (Chellaiah, et al. J Biol. Chem. 2003, 278, 29086-97). Na/H exchange transport system activation (Kawaguchi, et al. Eur J. Pharmacol. 2000, 403, 203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a —($CH_2$)$_{1-6}$—O—($CH_2$)$_{0-6}$—, a —($CH_2$)$_{0-6}$—S—($CH_2$)$_{0-6}$- or a —($CH_2$)$_{0-6}$-linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—($C_0$-$C_{10}$) alkyl-heteroaryl substituted cyclohexyl derivatives useful for the treatment of microbial infections. JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[($C_1$-$C_6$)alkylene)]$_{0-1}$—Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I—X—Ar II" wherein X may be (CHR$_1$)$_m$—Z—(CHR$_1$)$_n$, e.g. Z—$CH_2$, wherein Z may be O, R$_1$ is hydrogen or alkyl, Ar I may be among others an optionally substituted isoquinolone and Ar II may be among others an optionally substituted C$_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group (CR$^e$R$^f$)$_p$OR$^{43}$ wherein p may be zero, and R$^{43}$ is e.g. a (C$_3$-C$_{10}$)cycloalkyl residue optionally substituted by NR$^{51}$R$^{52}$, wherein R$^{51}$ and R$^{52}$ may be hydrogen, (C$_1$-C$_6$) alkyl etc.; or R$^{43}$ is a group R$^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group (CR$^e$R$^f$)$_p$OR$^{43}$ wherein p may be zero, and R$^{43}$ is e.g. a (C$_3$-C$_{10}$)cycloalkyl residue optionally substituted by NR$^{51}$R$^{52}$, wherein R$^{51}$ and R$^{52}$ may be hydrogen, (C$_1$-C$_6$)alkyl etc.; or R$^{43}$ is a group R$^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 03/053330 (Ube) generically describes isoquinolone derivatives of the formula

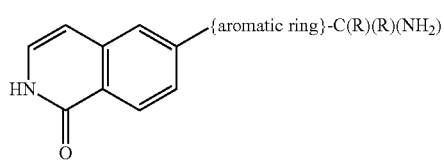

as Rho-kinase inhibitors.

WO 00/24718 (Akzo) describes inter alia 1-amino-isoquinoline derivatives for use as serine protease inhibitors which are substituted in the 6 position with a group —O—(CH2)m-E-D-J wherein m is one or two and E, D, J are as defined in the application.

EP-A-1 541 559 (Asahi) generically describes isoquinoline and isoquinolone derivatives substituted in the 5-position by a group R3 as Rho-kinase inhibitors.

SUMMARY OF THE INVENTION

An embodiment of the present invention is a compound of the formula (I)

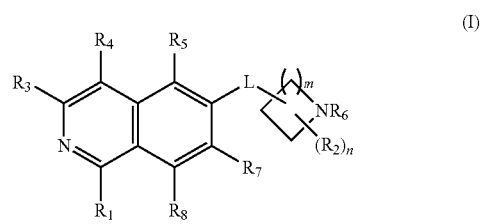

wherein
R$_1$ is H, OH or $NH_2$;
R$_2$ is hydrogen, halogen or (C$_1$-C$_6$)alkyl;
R$_3$ is
H,
halogen,
(C$_1$-C$_6$)alkyl,
(C$_1$-C$_6$)alkylene-R',
OH,
O—R",
$NH_2$,
NHR",
NR"R" or
NH—C(O)—R",
R$_4$ is
H,
halogen,
hydroxy,
CN,
(C$_1$-C$_6$)alkyl,
R',
(C$_1$-C$_6$)alkylene-R';
R$_5$ is
H,
halogen,
CN,
$NO_2$,
(C$_1$-C$_6$)alkyl,
(C$_2$-C$_6$)alkenyl,
R',
(C$_1$-C$_6$)alkylene-(C$_6$-C$_{10}$)aryl,
(C$_1$-C$_6$)alkenylene-(C$_6$-C$_{10}$)aryl,
(C$_1$-C$_6$)alkylene-(C$_5$-C$_{10}$)heterocyclyl,
CH(OH)—(C$_1$-C$_6$)alkyl,
$NH_2$,
NH—R',
NH—$SO_2$H,
NH—$SO_2$—(C$_1$-C$_6$)alkyl,
NH—$SO_2$—R',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_6$ is
H,
R', ($C_1$-$C_8$)alkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)NH$_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$;
($C_1$-$C_6$)alkylene-C(O)O—($C_1$-$C_6$)alkyl,
C(O)O—($C_1$-$C_6$)alkyl,
C(O)OR'
C(O)($C_1$-$C_6$)alkyl,
C(O)R',
C(O)NH—($C_1$-$C_6$)alkyl,
C(O)NHR',
C(O)N[($C_1$-$C_6$)alkyl]R'
C(O)N[($C_1$-$C_6$)alkyl]$_2$,
C(O)—($C_1$-$C_6$)alkylene-R', or
C(O)O($C_1$-$C_6$)alkylene-R';
$R_7$ is
H,
halogen,
CN,
NO$_2$,
($C_1$-$C_6$)alkyl,
O—($C_1$-$C_6$)alkyl,
($C_2$-$C_6$)alkenyl,
R',
($C_1$-$C_6$)alkenylene-($C_6$-$C_{10}$)aryl,
($C_1$-$C_6$)alkylene-R',
CH(OH)—($C_1$-$C_6$)alkyl,
NH$_2$,
NH—R',
NH—SO$_2$H,
NH—SO$_2$—($C_1$-$C_6$)alkyl,
NH—SO$_2$—R',
SO$_2$—NH$_2$,
SO$_2$—NHR',
NH—C(O)—($C_1$-$C_6$)alkyl,
NH—C(O)—R',
C(O)N[($C_1$-$C_6$)alkyl]$_2$,
C(O)OH, or
C(O)O—($C_1$-$C_6$)alkyl;
$R_8$ is H, halogen or ($C_1$-$C_6$)alkyl;
n is 1, 2, 3 or 4;
m is 1, 2, 3, 4 or 5; and
L is O or O—($C_1$-$C_6$)alkylene;
wherein
R' is
($C_3$-$C_8$)cycloalkyl,
($C_5$-$C_{10}$)heterocyclyl,
($C_6$-$C_{10}$)aryl;
R" is
($C_3$-$C_8$)cycloalkyl,
($C_5$-$C_{10}$)heterocyclyl,
($C_6$-$C_{10}$)aryl,
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R', or
($C_1$-$C_6$)alkylene-NR$_x$R$_y$; and
wherein R$_x$ and R$_y$ are independently of each other
($C_1$-$C_6$)alkyl,
($C_5$-$C_{10}$)heterocyclyl,
($C_6$-$C_{10}$)aryl,
($C_1$-$C_4$)alkylene-($C_5$-$C_{10}$)heterocyclyl,
($C_1$-$C_4$)alkylene-($C_6$-$C_{10}$)aryl,
($C_1$-$C_4$)alkylene-NH($C_1$-$C_6$)alkyl,
($C_1$-$C_4$)alkylene-N[($C_1$-$C_6$)alkyl]$_2$,
($C_1$-$C_4$)alkylene-N[($C_6$-$C_{10}$)aryl]$_2$, or
($C_1$-$C_4$)alkylene-N[($C_5$-$C_{10}$)heterocyclyl]$_2$;
wherein in residues $R_4$, $R_5$, $R_6$, $R_7$ and $R_8$ alkyl, alkylene or cycloalkyl can optionally be substituted one or more times by OH, OCH$_3$, COOH, COOCH$_3$, NH$_2$, NHCH$_3$, N(CH$_3$)$_2$, CONHCH$_3$ or CON(CH$_3$)$_2$;
wherein in residues $R_2$ to $R_8$ alkyl or alkylene can optionally be substituted one or more times by halogen;
wherein in residues $R_3$ to $R_8$ ($C_6$-$C_{10}$)aryl and ($C_5$-$C_{10}$)heterocyclyl are unsubstituted or substituted one or more times by suitable groups independently selected from halogen, OH, NO$_2$, N$_3$, CN, C(O)—($C_1$-$C_6$)alkyl, C(O)—($C_1$-$C_6$)aryl, COOH, COO($C_1$-$C_6$)alkyl, CONH$_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-NH$_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, PO$_3$H$_2$, SO$_3$H, SO$_2$—NH$_2$, SO$_2$NH($C_1$-$C_6$)alkyl, SO$_2$N[($C_1$-$C_6$)alkyl]$_2$, S—($C_1$-$C_6$)alkyl, SO—($C_1$-$C_6$)alkyl, SO$_2$—($C_1$-$C_6$)alkyl, SO$_2$—N=CH—N[($C_1$-$C_6$)alkyl]$_2$,
C(NH)(NH$_2$), NH$_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—SO$_2$—($C_1$-$C_6$)alkyl, NH—SO$_2$—($C_6$-$C_{10}$)aryl, NH—SO$_2$—($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl],
($C_6$-$C_{10}$)aryl, ($C_1$-$C_6$)alkylene-($C_6$-$C_{10}$)aryl, O—($C_6$-$C_{10}$)aryl,
O—($C_1$-$C_6$)alkylene-($C_6$-$C_{10}$)aryl, ($C_5$-$C_{10}$)heterocyclyl, ($C_1$-$C_6$)alkylene-($C_6$-$C_{10}$)heterocyclyl, or O—($C_1$-$C_6$)alkylene-($C_6$-$C_{10}$)heterocyclyl, wherein the ($C_6$-$C_{10}$)aryl or ($C_5$-$C_{10}$)heterocyclyl may be substituted one to three times by a group independently selected from halogen, OH, NO$_2$, CN, O—($C_1$-$C_6$)alkyl, ($C_1$-$C_6$)alkyl, NH$_2$, NH($C_1$-$C_6$)alkyl, N[($C_1$-$C_6$)alkyl]$_2$, SO$_2$CH$_3$, COOH, C(O)O—($C_1$-$C_6$)alkyl, CONH$_2$, ($C_1$-$C_6$)alkylene-O—($C_1$-$C_6$)alkyl, ($C_1$-$C_6$)alkylene-O—($C_6$-$C_{10}$)aryl, or O—($C_1$-$C_6$)alkylene-($C_6$-$C_{10}$)aryl;
or wherein ($C_6$-$C_{10}$)aryl is vicinally substituted by a O—($C_1$-$C_4$)alkylene-0 group whereby a 5-8-membered ring is formed together with the carbon atoms the oxygen atoms are attached to;
and wherein aryl or heterocyclyl substituents of ($C_6$-$C_{10}$)aryl and ($C_5$-$C_{10}$)heterocyclyl groups may not be further substituted by an aryl or heterocyclyl containing group;
and wherein, if m is 3, $R_6$ is not H, ($C_5$-$C_{10}$)heterocyclyl or ($C_6$-$C_{10}$)aryl; and
wherein, if m is 3 and $R_6$ is a residue selected from
($C_1$-$C_8$)alkyl,
($C_3$-$C_8$)cycloalkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)NH$_2$,
($C_1$-$C_6$)alkylene-C(O)NH—R', or
($C_1$-$C_6$)alkylene-C(O)N[R']$_2$;

alkyl, alkylene or cycloalkyl in said residue is substituted one or more times, preferably one to three times, by OH, OCH$_3$, COOH, COOCH$_3$, NH$_2$, NHCH$_3$, N(CH$_3$)$_2$, CONHCH$_3$ or CON(CH$_3$)$_2$;
or their stereoisomeric forms and/or their tautomeric forms and/or their pharmaceutically acceptable salts.

DETAILED DESCRIPTION OF THE INVENTION

Definitions

In a preferred embodiment of the present invention R$_1$ is H, the compound is thus characterized by the formula (II)

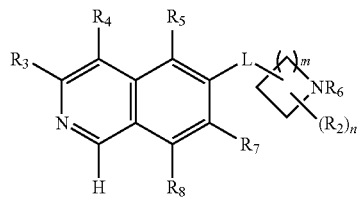

(II)

In another embodiment R$_1$ is OH, the compound is thus characterized by the formula

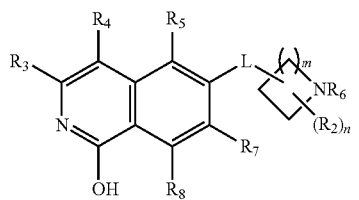

(III)

The compound of formula (III) has a tautomeric form of the formula (III')

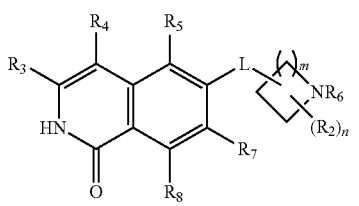

(III')

The tautomeric form is also an embodiment of the present invention.

In a further embodiment R$_1$ is NH$_2$ and the compound has the formula (IV)

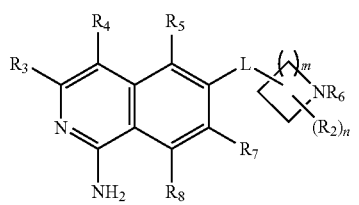

(IV)

R$_1$ is preferably H or OH.

R$_3$ is preferably H, halogen, (C$_1$-C$_4$)alkylene-R', O—R" or NHR". More preferred, R$_3$ is H or NHR". Most preferred, R$_3$ is H, NH—(C$_5$-C$_6$)heterocyclyl or NH-phenyl, especially preferred are H, NH—(C$_5$-C$_6$)heteroaryl containing one or more N atoms or NH-phenyl. Most especially preferred, R$_3$ is H.

Examples of R$_3$ substituents are

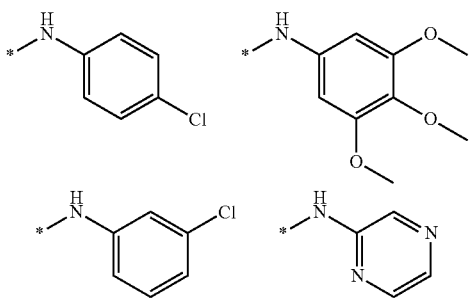

Preferably, R$_4$ is H, halogen or (C$_1$-C$_6$)alkyl. More preferred, R$_4$ is H, halogen or (C$_1$-C$_4$)alkyl. Most preferred, R$_4$ is H.

Preferably, R$_5$ is H, halogen, CN, (C$_1$-C$_6$)alkyl, (C$_2$-C$_6$)alkenyl, R', NH—(C$_6$-C$_{10}$)aryl or (C$_1$-C$_6$)alkylene-R'. More preferably, R$_5$ is H, halogen, (C$_1$-C$_6$)alkyl, (C$_2$-C$_6$)alkenyl, R', NH—(C$_6$-C$_{10}$)aryl or (C$_1$-C$_6$)alkylene-R'. Most preferably, R$_5$ is H, halogen, (C$_1$-C$_6$)alkyl, (C$_2$-C$_6$)alkenyl, (C$_6$-C$_{10}$)aryl, NH—(C$_6$-C$_{10}$)aryl, (C$_1$-C$_2$)alkyl-(C$_6$-C$_{10}$)aryl or (C$_5$-C$_{10}$)heteroaryl. Especially preferred, R$_5$ is H, halogen, phenyl, (C$_1$-C$_6$)alkyl, (C$_2$-C$_6$)alkenyl, (C$_6$-C$_{10}$)aryl or (C$_5$-C$_6$)heteroaryl. Most especially preferred R$_5$ is H, halogen, methyl, ethyl, vinyl, phenyl, thienyl or pyridyl.

Examples of R$_5$ are hydrogen, fluoro, chloro, bromo, iodo, methyl, ethyl, vinyl, phenyl, thienyl or pyridyl, nitrile, nitro, (p-methoxy)-phenyl, N-aniline, benzyl, 2-propenyl, s-butenyl, cyclopropyl, tetrazol, amino, 4-methoxy-aniline or N-acetyl, preferably hydrogen, fluoro, chloro, bromo, iodo, methyl, ethyl, vinyl, phenyl, thienyl or pyridyl. More preferred, R$_5$ is H, halogen, methyl, or ethyl, most preferred R$_5$ is H.

Preferably, R$_6$ is H, (C$_1$-C$_6$)alkyl, R', (C$_1$-C$_4$)alkylene-(C$_5$-C$_{10}$)aryl, (C$_1$-C$_4$)alkylene-(C$_3$-C$_8$)cycloalkyl, (C$_1$-C$_4$)alkylene-(C$_5$-C$_{10}$)heterocyclyl, (C$_1$-C$_6$)alkylene-O—(C$_1$-C$_6$)alkyl, (C$_1$-C$_4$)alkylene-C(O)—(C$_5$-C$_{10}$)heterocyclyl, (C$_1$-C$_4$)alkylene-C(O)—(C$_6$-C$_{10}$)aryl, (C$_1$-C$_6$)alkylene-C(O)N[(C$_1$-C$_6$)alkyl]$_2$, (C$_1$-C$_6$)alkylene-C(O)NH—(C$_1$-C$_6$)alkyl, (C$_1$-C$_6$)alkylene-C(O)O—(C$_1$-C$_6$)alkyl, C(O)O—(C$_1$-C$_6$)alkyl, C(O)(C$_1$-C$_6$)alkyl, C(O)R', C(O)NH—(C$_1$-C$_6$)alkyl, C(O)N[(C$_1$-C$_6$)alkyl]$_2$, or C(O)(C$_1$-C$_6$)alkylene-R'.

In a further preferred embodiment R$_6$ is H, (C$_1$-C$_6$)alkyl, (C$_5$-C$_{10}$)heterocyclyl, (C$_3$-C$_8$)cycloalkyl, (C$_6$-C$_{10}$)aryl, (C$_1$-C$_4$)alkylene-(C$_3$-C$_8$)cycloalkyl, (C$_1$-C$_4$)alkylene-(C$_5$-C$_{10}$)heterocyclyl, (C$_1$-C$_4$)alkylene-(C$_6$-C$_{10}$)aryl, (C$_1$-C$_6$)alkylene-O—(C$_1$-C$_6$)alkyl, (C$_1$-C$_6$)alkylene-C(O)N[(C$_1$-C$_6$)alkyl]$_2$, (C$_1$-C$_6$)alkylene-C(O)NH—(C$_1$-C$_6$)alkyl, (C$_1$-C$_6$)alkylene-C(O)O—(C$_1$-C$_6$)alkyl, C(O)O—(C$_1$-C$_6$)alkyl, C(O)(C$_1$-C$_6$)alkyl, C(O)—(C$_5$-C$_{10}$)heterocyclyl, C(O)(C$_3$-C$_8$)cycloalkyl, C(O)NH—(C$_1$-C$_6$)alkyl, C(O)N[(C$_1$-C$_6$)alkyl]$_2$, C(O) (C$_1$-C$_6$)alkylene-(C$_3$-C$_8$)cycloalkyl, C(O) (C$_1$-C$_6$)alkylene-C$_5$-C$_{10}$)heterocyclyl, or C(O)(C$_1$-C$_6$)alkylene-(C$_6$-C$_{10}$)aryl:

In a further more preferred embodiment R$_6$ is H, (C$_1$-C$_6$)alkyl, (C$_3$-C$_8$)cycloalkyl, (C$_5$-C$_{10}$)heterocyclyl, (C$_5$-C$_{10}$)aryl, (C$_1$-C$_4$)alkylene-(C$_3$-C$_8$)cycloalkyl, (C$_1$-C$_4$)alkylene-(C$_5$-C$_{10}$)heterocyclyl, (C$_1$-C$_4$)alkylene-(C$_6$-C$_{10}$)aryl, (C$_1$-C$_6$)alkylene-O—(C$_1$-C$_6$)alkyl, (C$_1$-C$_6$)alkylene-C(O)NH—(C$_1$-C$_6$)alkyl, (C$_1$-C$_6$)alkylene-C(O)N[(C$_1$-C$_6$)alkyl]$_2$, C(O)O—(C$_1$-C$_6$)alkyl, C(O)(C$_1$-C$_6$)alkyl, C(O)(C$_3$-C$_8$)cycloalkyl, C(O)—(C$_5$-C$_{10}$)heterocyclyl, C(O)NH—(C$_1$-C$_6$)alkyl, C(O)N[(C$_1$-C$_6$)alkyl]$_2$, C(O)(C$_1$-C$_6$)alkylene-(C$_3$-

$C_8$)cycloalkyl, $C(O)(C_1-C_6)$alkylene-$(C_5-C_{10})$heterocyclyl, or $C(O)(C_1-C_6)$alkylene-$(C_6-C_{10})$aryl.

In an more preferred embodiment $R_6$ is H, $(C_1-C_6)$alkyl, $(C_3-C_8)$cycloalkyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_4)$alkylene-$O$—$(C_1-C_4)$alkyl, $C(O)(C_1-C_6)$alkyl, $C(O)(C_3-C_8)$cycloalkyl, $C(O)$—$(C_5-C_{10})$heterocyclyl, $C(O)(C_1-C_4)$alkylene-$(C_5-C_{10})$heterocyclyl, or $C(O)(C_1-C_4)$alkylene-$(C_6-C_{10})$aryl.

In an even more preferred embodiment $R_6$ is

H, $(C_1-C_6)$alkyl, $(C_3-C_8)$cycloalkyl;

$(C_1-C_4)$alkylene-$(C_3-C_8)$cycloalkyl;

$(C_1-C_4)$alkylene-$(C_5-C_{10})$heterocyclyl wherein heterocyclyl is unsubstituted or substituted one or more times, preferably one or two times, by $(C_1-C_4)$alkyl;

$(C_1-C_4)$alkylene-$(C_6-C_{10})$aryl wherein aryl is unsubstituted or substituted one or more times, preferably one to three times, by halogen, $(C_1-C_4)$alkyl especially $CH_3$ or $CF_3$, $O$—$(C_1-C_4)$alkyl especially $OCH_3$, $SO_2$—$(C_1-C_4)$alkyl especially $S(O)_2CH_3$ or $SO_2CF_3$, or $SO_2$—$N=CH$—$N[(C_1-C_6)$alkyl$]_2$ especially $SO_2$—$N=CH$—$N(CH_3)_2$;

$C(O)(C_1-C_6)$alkyl, preferably $C(O)(C_1-C_4)$alkyl, $C(O)(C_3-C_6)$cycloalkyl, $C(O)$—$(C_5-C_6)$heterocyclyl wherein the heterocyclyl is unsubstituted;

$C(O)(C_1-C_4)$alkylene-$(C_5-C_{10})$heterocyclyl wherein the heterocyclyl is unsubstituted; or $C(O)(C_1-C_4)$alkylene-$(C_6-C_{10})$aryl wherein the aryl is unsubstituted or substituted one or more times, preferably one to three times, by halogen;

wherein a $(C_1-C_4)$alkyl or $(C_1-C_6)$alkyl residue is unsubstituted or substituted one to three times, preferably one or two times, by a group independently selected from OH, halogen, $NH_2$, $NH(CH_3)$ or $N(CH_3)_2$, a $(C_1-C_4)$alkylene residue is unsubstituted or substituted once by amino or $N(CH_3)_2$ and a $(C_3-C_8)$cycloalkyl residue is unsubstituted or substituted once by $NH_2$.

In another especially preferred embodiment R6 is $(C_1-C_6)$alkylene-$C(O)NH_2$, $(C_1-C_6)$alkylene-$C(O)NH$—$(C_1-C_6)$alkyl, $(C_1-C_6)$alkylene-$C(O)N[(C_1-C_6)$alkyl$]_2$, $C(O)(C_1-C_6)$alkyl, preferably $C(O)(C_1-C_4)$alkyl, $C(O)(C_3-C_6)$cycloalkyl, wherein the cycloalkyl is unsubstituted or substituted once by $NH_2$, $C(O)$—$(C_5-C_6)$heterocyclyl wherein the heterocyclyl is unsubstituted;

$C(O)(C_1-C_4)$alkylene-$(C_5-C_{10})$heterocyclyl wherein the heterocyclyl is unsubstituted;

$C(O)(C_1-C_4)$alkylene-$(C_6-C_{10})$aryl wherein the aryl is unsubstituted or substituted one or more times, preferably one to three times, by halogen;

wherein a $(C_1-C_4)$alkyl or $(C_1-C_6)$alkyl residue is unsubstituted or substituted one to three times, preferably one or two times, by a group independently selected from OH, halogen, $NH_2$, $NH(CH_3)$ or $N(CH_3)_2$, a $(C_1-C_4)$alkylene residue is unsubstituted or substituted once by amino, $NH(CH_3)$ or $N(CH_3)_2$; or is $(C_1-C_6)$alkyl, wherein alkyl is substituted once with amino.

More preferred R6 is $C(O)(C_1-C_6)$alkyl, preferably $C(O)(C_1-C_4)$alkyl, wherein the alkyl is unsubstituted or, preferably, substituted one to three times, preferably one or two times, most preferably once, by a group independently selected from OH, halogen, $NH_2$, $NH(CH_3)$ or $N(CH_3)_2$;

$C(O)$—$(C_5-C_6)$heterocyclyl wherein the heterocyclyl is unsubstituted;

$C(O)$—$(C_3-C_6)$cycloalkyl, wherein cycloalkyl is unsubstituted or substituted by amino, or $C(O)(C_1-C_4)$alkylene-$(C_6-C_{10})$aryl wherein the aryl is phenyl which is unsubstituted or substituted one or more times, preferably one to three times, more preferably once, by halogen and wherein the alkylene is unsubstituted or, preferably, substituted once by amino, $NH(CH_3)$ or $N(CH_3)_2$.

Especially preferred $R_6$ is H, $(C_1-C_6)$alkyl or $(C_3-C_8)$cycloalkyl. In an even more especially preferred embodiment $R_6$ is H, preferably unsubstituted $(C_1-C_6)$alkyl or preferably unsubstituted $(C_3-C_8)$cycloalkyl. Most preferred $R_6$ is H.

In a embodiment of a compound of formula (I) $R_6$ is not tert-butyloxycarbonyl.

As examples for these embodiments, $R_6$ is hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

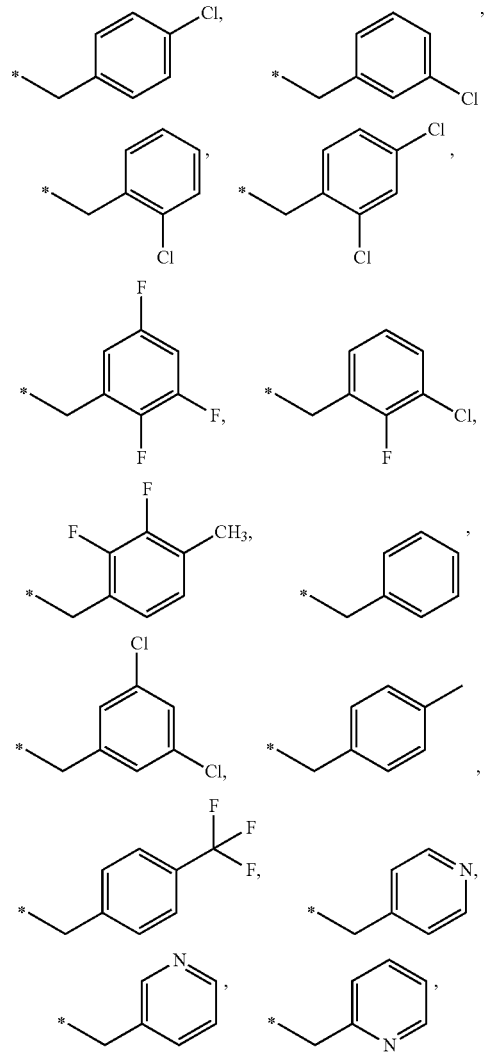

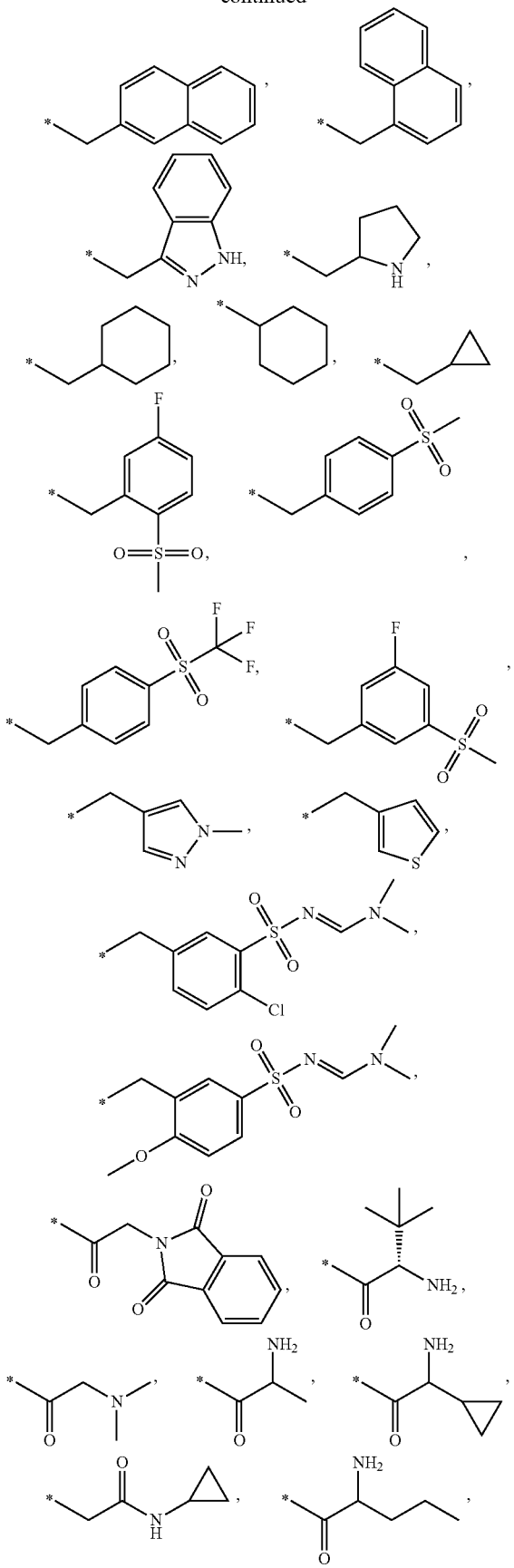

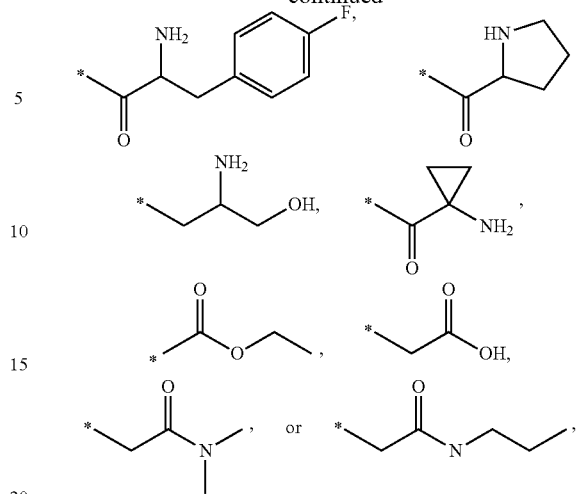

Other R6 examples are

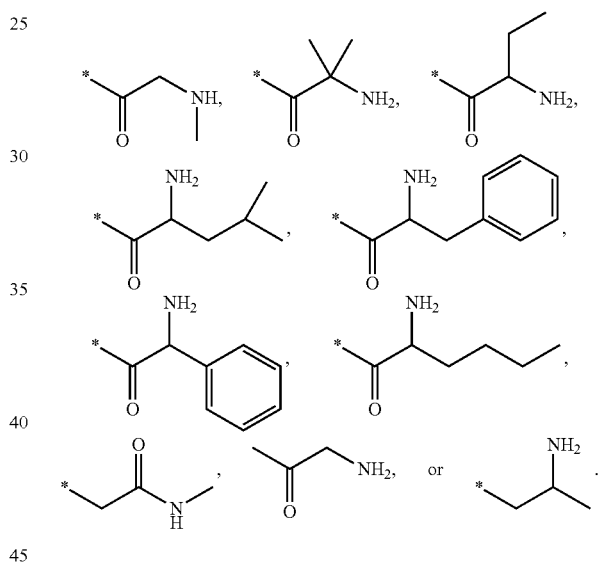

The asterisk (*) denotes where the bond is connected to the N-atom of the ring.

Preferably, $R_7$ is H, halogen, CN, $(C_1-C_8)$alkyl, $O-(C_1-C_8)$alkyl, $(C_2-C_8)$alkenyl, R' or $(C_1-C_8)$alkylene-$(C_3-C_8)$cycloalkyl. More preferred, $R_7$ is H, halogen, CN, $(C_1-C_4)$alkyl, $O-(C_1-C_4)$alkyl, $(C_1-C_4)$alkenyl, phenyl, cyclopropyl or $(C_5-C_8)$heteroaryl. Most preferably, $R_7$ is H, fluoro, chloro, bromo, methyl, ethyl, methoxy, propyl, phenyl, nitrile, cyclopropyl, thienyl or vinyl, most especially preferred $R_7$ is H, fluoro, chloro, bromo, methyl, propyl or methoxy. Most preferred $R_7$ is H.

$R_8$ is preferably H, halogen or $(C_1-C_4)$alkyl. More preferred, $R_8$ is H, Cl, F, methyl or ethyl. Most preferred $R_8$ is H.

Preferably, $R_2$ is H, halogen or $(C_1-C_4)$alkyl. Preferably, $R_2$ is H or $(C_1-C_2)$alkyl. More preferred, $R_2$ is H, methyl or ethyl. Most preferred $R_2$ is H. $R_2$ may be bound to any carbon atom of the ring including the position where the linker group L is bound.

Preferably, n is 1, 2 or 3. More preferred, n is 1 or 2. Most preferred n is 1.

Preferably m is 2, 3 or 4. More preferred m is 3. In another embodiment m is 1, 2, 4 or 5.

The linker group L may be bound to the ring in any position via a ring carbon atom. In a preferred embodiment, m is 3 and L is attached to the 4-position of the piperidine ring

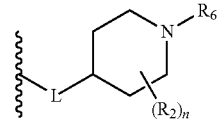

or L is attached to the 3-position of the piperidine ring

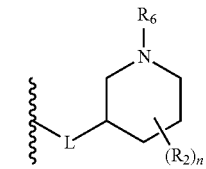

In an especially preferred embodiment, L is attached to the 4-position of the piperidine ring.

In a further preferred embodiment, L is O-methylene, O-ethylene or preferably O. In another preferred embodiment L is O-methylene or O. More preferably, m is 3 and L is O-methylene, O-ethylene or O attached to the 4-position of the piperidine ring.

In residues $R_2$ to $R_8$ an alkyl or alkylene can optionally be substituted one or more times by halogen. Preferably alkyl or alkylene is substituted one to three times by halogen selected from chloro or bromo but may be substituted by fluoro once or more, e.g. being perfluorinated. Preferably halogen is Fluor. More preferred an alkyl or alkylene is not halogenated.

In residues $R_4$, $R_5$, $R_6$, $R_7$ and $R_8$ alkyl, alkylene or cycloalkyl can optionally be substituted one or more times by a group selected independently from OH, $OCH_3$, COOH, $COOCH_3$, $NH_2$, $NHCH_3$, $N(CH_3)_2$, $CONHCH_3$ or $CON(CH_3)_2$.

If substituted, the number of substituents is preferably between 1, 2, 3 or 4, more preferably 1 or 2 with 1 being even more preferred. Preferably an alkylene or cycloalkyl is not substituted. More preferably an alkyl, alkylene or cycloalkyl is not substituted. Preferably in $R_4$, $R_5$, $R_7$ and $R_8$ an alkyl, alkylene or cycloalkyl is not substituted. More preferred, in $R_4$, $R_5$, $R_6$, $R_7$ and $R_8$ an alkyl, alkylene or cycloalkyl is not substituted.

In preferred embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

The term "*-" in the exemplified substituents vide supra marks the point where the substituent is attached, which means, for example, for a $R_3$ substituent

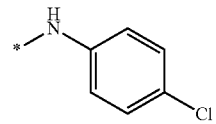 [SMILES: *Nc1ccc(Cl)cc1]

and m is 3 and R1 is H a compound of the formula

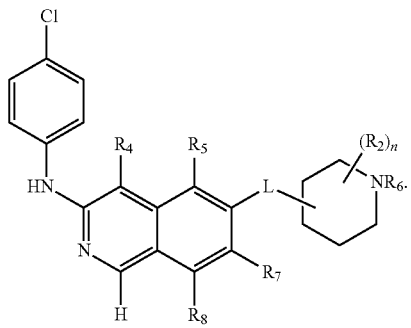

A preferred embodiment is a compound of the formula (I) wherein
$R_1$ is H or OH;
$R_2$ is hydrogen, halogen, or $(C_1-C_6)$alkyl;
$R_3$ is H, halogen, $(C_1-C_4)$alkylene-R', O—R" or NHR";
$R_4$ is H, halogen or $(C_1-C_6)$alkyl;
$R_5$ is H, $(C_1-C_6)$alkyl, halogen, CN, $(C_2-C_6)$alkenyl, $(C_6-C_{10})$aryl, NH—$(C_6-C_{10})$aryl, $(C_1-C_6)$alkylene-$(C_6-C_{10})$aryl, $(C_5-C_{10})$heterocyclyl or $(C_1-C_6)$alkylene-$(C_5-C_{10})$heterocyclyl;
$R_6$ is H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)$NH_2$, $(C_1-C_6)$alkylene-C(O)NH—R', $(C_1-C_6)$alkylene-C(O)N[$(C_1-C_4)$alkyl]$_2$, C(O)$(C_1-C_4)$alkyl or $(C_1-C_6)$alkylene-C(O)N[R']$_2$,
C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$alkyl]$_2$, C(O)$(C_1-C_6)$alkylene-$C_3-C_8)$cycloalkyl, C(O) $(C_1-C_6)$alkylene-$C_5-C_{10})$heterocyclyl or C(O) $(C_1-C_6)$alkylene-$(C_6-C_{10})$aryl.
$R_7$ is H, halogen, CN, $(C_1-C_6)$alkyl, O—$(C_1-C_6)$alkyl, $(C_2-C_6)$alkenyl or R';
$R_8$ is H, halogen or $(C_1-C_6)$alkyl;
m is 2, 3 or 4
n is 1, 2 or 3, and
L is O,O-methylene or O-ethylene;
or their stereoisomeric and/or tautomeric forms and/or their pharmaceutically acceptable salts.

A further preferred embodiment is a compound of the formula (I) wherein
$R_1$ is H or OH;
$R_2$ is H or $(C_1-C_4)$alkyl;
$R_3$ is H, halogen or NHR", wherein R" is defined as above;
$R_4$ is H, halogen or $(C_1-C_4)$alkyl;
$R_5$ is H, $(C_1-C_6)$alkyl, halogen, $(C_2-C_4)$alkenyl, $(C_6-C_{10})$aryl, $(C_1-C_6)$alkylene-$(C_6-C_{10})$aryl or $(C_5-C_{10})$heterocyclyl;
$R_6$ is H, $(C_3-C_8)$cycloalkyl, $(C_1-C_8)$alkyl, $(C_1-C_6)$alkylene-O—$(C_1-C_6)$alkyl, $(C_1-C_3)$alkylene-R', C(O)O—$(C_1-C_6)$alkyl, C(O)$(C_1-C_6)$alkyl, C(O)$(C_3-C_8)$cycloalkyl, C(O)—$(C_5-C_{10})$heterocyclyl, C(O)NH—$(C_1-C_6)$alkyl, C(O)N [$(C_1-C_6)$alkyl]$_2$, C(O)$(C_1-C_3)$alkylene-$(C_3-C_8)$cycloalkyl, C(O)$(C_1-C_3)$alkylene-$(C_5-C_{10})$heterocyclyl, or C(O)$(C_1-C_3)$alkylene-$(C_6-C_{10})$aryl;

R₇ is H, halogen, CN, $(C_1-C_6)$alkyl, $O(C_1-C_6)$alkyl, $(C_2-C_6)$alkenyl or R';
R₈ is H, halogen or $(C_1-C_6)$alkyl;
m is 2, 3 or 4
n is 1, 2 or 3; and
L is O;
or their stereoisomeric and/or tautomeric forms and/or their pharmaceutically acceptable salts.

An especially preferred embodiment is a compound of the formula (I) wherein
R₁ is H or OH;
R₂ is H, $(C_1-C_4)$alkyl;
R₃ is H, NH—$(C_5-C_6)$heteroaryl or NH-phenyl;
R₄ is H, halogen or $(C_1-C_4)$alkyl;
R₅ is H, $(C_1-C_4)$alkyl, halogen, $(C_1-C_4)$alkenyl, $(C_6-C_{10})$aryl, $(C_1-C_2)$alkyl-$(C_6-C_{10})$aryl or $(C_5-C_6)$heteroaryl;
R₆ is H, $(C_3-C_8)$cycloalkyl, $(C_1-C_8)$alkyl, $(C_1-C_3)$alkylene-R'; $C(O)(C_1-C_6)$alkyl, $C(O)(C_3-C_8)$cycloalkyl, $C(O)$—$(C_5-C_{10})$heterocyclyl, $C(O)(C_1-C_3)$alkylene-$(C_5-C_{10})$heterocyclyl, or $C(O)(C_1-C_3)$alkylene-$(C_6-C_{10})$aryl.
R₇ is H, halogen, CN, $(C_1-C_4)$alkyl, $O(C_1-C_4)$alkyl, $(C_1-C_4)$alkenyl, phenyl, cyclopropyl, $(C_5-C_6)$heteroaryl;
R₈ is H, halogen or $(C_1-C_4)$alkyl;
m is 3
n is 1; and
L is O;
or their stereoisomeric and/or tautomeric forms and/or their pharmaceutically acceptable salts.

In a embodiment a compound of formula (I) is not (2S)-1-tert-butoxycarbonyl-2-(2-(1-amino-isoquinolin-6-oxy) ethyl)-piperidine or (2S)-1-tert-butoxycarbonyl-2-(2-(1-amino-isoquinolin-6-oxy)ethyl)-pyrrolidine.

In another embodiment of a compound of formula (I) wherein
R1 is NH₂ or OH; R3 and R8 are H; R4 is H when R1 is NH₂ or R4 is H or bromo when R1 is OH; R5 is H; R7 is H or methyl; m is 2, 3, or 4; L is O;
R6 is not H, pyrrolyl, methyl, hydroxypropyl, or phenylmethyl wherein the phenyl group is unsubstituted or substituted by methanesulfonyl, methyl, fluoro, or methoxy.

In a further embodiment, the present invention relates to a compound of formula (I) selected from
8. 7-Chloro-6-[1-(2-methylamino-acetyl)-piperidin-4-yloxy]-2H-isoquinolin-1-one,
10. 6-[1-(2-Amino-3,3-dimethyl-butyryl)-piperidin-4-yloxy]-7-chloro-2H-isoquinolin-1-one,
11. 6-[1-(2-Amino-propionyl)-piperidin-4-yloxy]-7-chloro-2H-isoquinolin-1-one,
12. 6-[1-(2-Amino-2-methyl-propionyl)-piperidin-4-yloxy]-7-chloro-2H-isoquinolin-1-one
13. 6-[1-((S)-2-Amino-butyryl)-piperidin-4-yloxy]-7-chloro-2H-isoquinolin-1-one,
14. 6-[1-((S)-2-Amino-4-methyl-pentanoyl)-piperidin-4-yloxy]-7-chloro-2H-isoquinolin-1-one,
15. 7-Chloro-6-[1-((S)-pyrrolidine-2-carbonyl)-piperidin-4-yloxy]-2H-isoquinolin-1-one,
16. 7-Chloro-6-[1-(2-dimethylamino-acetyl)-piperidin-4-yloxy]-2H-isoquinolin-1-one,
17. 6-[1-((S)-2-Amino-propionyl)-piperidin-4-yloxy]-7-chloro-2H-isoquinolin-1-one,
18. 6-[1-((S)-2-Amino-2-phenyl-acetyl)-piperidin-4-yloxy]-7-chloro-2H-isoquinolin-1-one,
19. 6-[1-(1-Amino-cyclopropanecarbonyl)-piperidin-4-yloxy]-7-chloro-2H-iso quinolin-1-one,
20. 6-[1-((S)-2-Amino-pentanoyl)-piperidin-4-yloxy]-7-chloro-2H-isoquinolin-1-one,
22. 6-{1-[(S)-2-Amino-3-(4-chloro-phenyl)-propionyl]-piperidin-4-yloxy}-7-chloro-2H-isoquinolin-1-one,
23. 6-{1-[(S)-2-Amino-3-(4-fluoro-phenyl)-propionyl]-piperidin-4-yloxy}-7-chloro-2H-isoquinolin-1-one,
24. 6-[1-(2-Amino-acetyl)-piperidin-4-yloxy]-2H-isoquinolin-1-one,
25. 6-[1-((R)-2-Amino-pentanoyl)-piperidin-4-yloxy]-2H-isoquinolin-1-one,
26. 6-[1-((S)-2-Amino-4-methyl-pentanoyl)-piperidin-4-yloxy]-2H-isoquinolin-1-one,
27. 6-{1-[(S)-2-Amino-3-(4-chloro-phenyl)-propionyl]-piperidin-4-yloxy}-2H-isoquinolin-1-one,
28. 6-[1-(2-Methylamino-acetyl)-piperidin-4-yloxy]-2H-isoquinolin-1-one
29. 6-[1-((S)-Pyrrolidine-2-carbonyl)-piperidin-4-yloxy]-2H-isoquinolin-1-one,
30. 6-[1-((S)-2-Amino-3,3-dimethyl-butyryl)-piperidin-4-yloxy]-2H-isoquinolin-1-one,
31. 6-[1-((S)-2-Amino-butyryl)-piperidin-4-yloxy]-2H-isoquinolin-1-one,
32. 6-[1-((S)-2-Amino-propionyl)-piperidin-4-yloxy]-2H-isoquinolin-1-one,
34. 6-[1-((R)-2-Amino-propionyl)-piperidin-4-yloxy]-2H-isoquinolin-1-one,
35. 6-[1-((S)-2-Amino-2-phenyl-acetyl)-piperidin-4-yloxy]-2H-isoquinolin-1-one,
36. 6-[1-((S)-2-Amino-hexanoyl)-piperidin-4-yloxy]-2H-isoquinolin-1-one,
37. 6-[1-((S)-2-Amino-4-methyl-pentanoyl)-piperidin-4-yloxy]-2H-isoquinolin-1-one,
38. 6-{1-[(S)-2-Amino-3-(4-fluoro-phenyl)-propionyl]-piperidin-4-yloxy}-2H-isoquinolin-1-one,
39. 6-[1-(2-Amino-2-methyl-propionyl)-piperidin-4-yloxy]-2H-isoquinolin-1-one, or
40. 6-[1-(2-Amino-acetyl)-piperidin-4-yloxy]-7-chloro-2H-isoquinolin-1-one,
or their stereoisomeric and/or tautomeric forms and/or their pharmaceutically acceptable salts.

in another embodiment the present invention relates to a compound of formula (I) selected from
41. [4-(7-Chloro-1-oxo-1,2-dihydro-isoquinolin-6-yloxy)-piperidin-1-yl]-acetic acid ethyl ester,
42. [4-(7-Chloro-1-oxo-1,2-dihydro-isoquinolin-6-yloxy)-piperidin-1-yl]-acetic acid,
43. 2-[4-(7-Chloro-1-oxo-1,2-dihydro-isoquinolin-6-yloxy)-piperidin-1-yl]-N,N-dimethyl-acetamide,
44. 2-[4-(7-Chloro-1-oxo-1,2-dihydro-isoquinolin-6-yloxy)-piperidin-1-yl]-N-ethyl-acetamide,
45. 2-[4-(7-Chloro-1-oxo-1,2-dihydro-isoquinolin-6-yloxy)-piperidin-1-yl]-N-methyl-acetamide, or
46. 2-[4-(7-Chloro-1-oxo-1,2-dihydro-isoquinolin-6-yloxy)-piperidin-1-yl]-N-propyl-acetamide,
or their stereoisomeric and/or tautomeric forms and/or their pharmaceutically acceptable salts.

In a further embodiment, the present invention relates to a compound of formula (I) selected from
52. 6-(Azepan-4-yloxy)-2H-isoquinolin-1-one,
53. 6-((R)-(Pyrrolidin-3-yloxy)-2H-isoquinolin-1-one,
54. 6-((S)-Pyrrolidin-3-yloxy)-2H-isoquinolin-1-one,
55. 6-(Azepan-4-yloxy)-7-chloro-2H-isoquinolin-1-one,
56. 6-((R)-Pyrrolidin-3-yloxy)-7-chloro-2H-isoquinolin-1-one,
57. 6-((S)-Pyrrolidin-3-yloxy)-7-chloro-2H-isoquinolin-1-one,
58. 6-(Azetidin-3-yloxy)-7-chloro-2H-isoquinolin-1-one,
59. 6-(Azepan-4-yloxy)-4,7-dimethyl-2H-isoquinolin-1-one, 60. 4,7-Dimethyl-6-((R)-pyrrolidin-3-yloxy)-2H-isoquinolin-1-one,
61. 4,7-Dimethyl-6-((S)-pyrrolidin-3-yloxy)-2H-isoquinolin-1-one,
62. 4,7-Dimethyl-6-(1-methyl-pyrrolidin-3-yloxy)-2H-isoquinolin-1-one,
64. 6-(1-Methyl-pyrrolidin-3-yloxy)-2H-isoquinolin-1-one,
66. 6-((R)-1-Benzyl-pyrrolidin-3-yloxy)-7-chloro-2H-isoquinolin-1-one
67. 6-((S)-1-Benzyl-pyrrolidin-3-yloxy)-7-chloro-2H-isoquinolin-1-one,
68. 6-(Azepan-4-yloxy)-7-methyl-2H-isoquinolin-1-one,
69. 7-Methyl-6-((R)-1-pyrrolidin-3-ylmethoxy)-2H-isoquinolin-1-one,
70. 7-Methyl-6-((S)-pyrrolidin-3-yloxy)-2H-isoquinolin-1-one, or
71. 7-Methyl-6-((R)-pyrrolidin-3-yloxy)-2H-isoquinolin-1-one,
more preferably
55. 6-(Azepan-4-yloxy)-7-chloro-2H-isoquinolin-1-one,
56. 6-((R)-Pyrrolidin-3-yloxy)-7-chloro-2H-isoquinolin-1-one,
57. 6-((S)-Pyrrolidin-3-yloxy)-7-chloro-2H-isoquinolin-1-one,
58. 6-(Azetidin-3-yloxy)-7-chloro-2H-isoquinolin-1-one,
59. 6-(Azepan-4-yloxy)-4,7-dimethyl-2H-isoquinolin-1-one,
60. 4,7-Dimethyl-6-((R)-pyrrolidin-3-yloxy)-2H-isoquinolin-1-one,
61. 4,7-Dimethyl-6-((S)-pyrrolidin-3-yloxy)-2H-isoquinolin-1-one,
62. 4,7-Dimethyl-6-(1-methyl-pyrrolidin-3-yloxy)-2H-isoquinolin-1-one,
66. 6-((R)-1-Benzyl-pyrrolidin-3-yloxy)-7-chloro-2H-isoquinolin-1-one
67. 6-((S)-1-Benzyl-pyrrolidin-3-yloxy)-7-chloro-2H-isoquinolin-1-one,
68. 6-(Azepan-4-yloxy)-7-methyl-2H-isoquinolin-1-one,
69. 7-Methyl-6-((R)-1-pyrrolidin-3-ylmethoxy)-2H-isoquinolin-1-one,
70. 7-Methyl-6-((S)-pyrrolidin-3-yloxy)-2H-isoquinolin-1-one, or
71. 7-Methyl-6-((R)-pyrrolidin-3-yloxy)-2H-isoquinolin-1-one,
or their stereoisomeric and/or tautomeric forms and/or their pharmaceutically acceptable salts.

In a further embodiment, the present invention relates to a compound of formula (I) selected from
72. 6-[1-((S)-2-Amino-propyl)-piperidin-3-yloxy]-2H-isoquinolin-1-one,
73. 6-[1-((S)-2-Amino-propyl)-piperidin-4-yloxy]-5-fluoro-4-methyl-2H-isoquinolin-1-one,
74. 6-[1-((R)-2-Amino-3-hydroxy-propyl)-piperidin-4-yloxy]-2H-isoquinolin-1-one, or
75. 6-[1-((R)-2-Amino-3-hydroxy-propyl)-piperidin-4-yloxy]-5-fluoro-4-methyl-2H-isoquinolin-1-one,
or their stereoisomeric and/or tautomeric forms and/or their pharmaceutically acceptable salts. (Numbering corresponding to Cpd./Example number)

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline substitution pattern is numbered according to IUPAC rules:

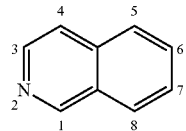

All references to "compound(s) of formula (I)" hereinafter refer to compound(s) of the formula (I), (II), (III), (III') and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I), (II), (III) or (III') in the form of their stereoisomeric forms, which include racemates, racemic mixtures, pure enantiomers and diastereomers and mixtures thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The terms $(C_1-C_2)$alkyl, $(C_1-C_4)$alkyl, $(C_1-C_6)$alkyl, $(C_1-C_8)$alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O($C_1-C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—$(CF_2)_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

Halogen means fluoro, chloro, bromo or iodo.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A $(C_6-C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

A $(C_5-C_{10})$heterocyclyl group means a mono- or bicyclic ring system in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. $(C_5-C_{10})$heterocyclyl groups may be (1) aromatic [=heteroaryl groups] or (2) saturated or (3) mixed aromatic/saturated.

Suitable $(C_5-C_{10})$heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heterocyclyl residues can occur on free carbon atoms or on nitrogen atoms.

Preferred examples of $(C_5-C_{10})$heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

$(C_6-C_{10})$aryl and $(C_5-C_{10})$heterocyclyl groups are unsubstituted or, if not stated otherwise, substituted one or more times, preferably one to three times, by suitable groups independently selected from halogen, OH, $NO_2$, $N_3$, CN, C(O)—$(C_1-C_6)$alkyl, C(O)—$(C_1-C_6)$aryl, COOH, COO$(C_1-C_6)$alkyl, $CONH_2$, CONH$(C_1-C_6)$alkyl, CON[$(C_1-C_6)$alkyl]$_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2NH(C_1-C_6)$alkyl, $SO_2N[(C_1-C_6)$alkyl]$_2$, S—$(C_1-C_6)$alkyl; SO—$(C_1-C_6)$alkyl, $SO_2$—$(C_1-C_6)$alkyl, $SO_2$—N=CH—N[$(C_1-C_6)$alkyl]$_2$, C(NH)($NH_2$), $NH_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$—$(C_5-C_{10})$heterocyclyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, 0-$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, O—$(C_1-C_6)$alkylene-$(C_5-C_{10})$heterocyclyl,
wherein the $(C_6-C_{10})$aryl or $(C_5-C_{10})$heterocyclyl may be substituted one to 3 times by a group independently selected from halogen, OH, $NO_2$, CN, O—$(C_1-C_6)$alkyl, $(C_1-C_6)$alkyl, $NH_2$, NH$(C_1-C_6)$alkyl, N[$(C_1-C_6)$alkyl]$_2$, $SO_2CH_3$, COOH, C(O)O—$(C_1-C_6)$alkyl, $CONH_2$, $(C_1-C_6)$alkylene-O—$(C_1-C_6)$alkyl, $(C_1-C_6)$alkylene-O—$(C_6-C_{10})$aryl, O—$(C_1-C_6)$alkylene-$(C_6-C_{10})$aryl; or wherein $(C_6-C_{10})$aryl is vicinally substituted by a O—$(C_1-C_4)$alkylene-0 group whereby a 5-8-membered ring is formed together with the carbon atoms the oxygen atoms are attached to. Aryl or heterocyclyl substituents of $(C_6-C_{10})$aryl and $(C_5-C_{10})$heterocyclyl groups may not be further substituted by an aryl or heterocyclyl containing group.

Preferred substituents for $(C_6-C_{10})$aryl groups are $(C_1-C_4)$alkyl, O—$(C_1-C_4)$alkyl, O-phenyl, phenyl, C(O)O—$(C_1-C_6)$alkyl, C(O)OH, C(O)—$(C_1-C_4)$alkyl, halogen, $NO_2$, $SO_2NH_2$, CN, $SO_2$—$(C_1-C_4)$alkyl, $SO_2$—N=CH—N[$(C_1$-$C_6)$alkyl]$_2$, NH—$SO_2$—$(C_1-C_4)$alkyl, $NH_2$, NH—C(O)—$(C_1-C_4)$alkyl, $(C_3-C_8)$cycloalkyl, $(C_1-C_4)$alkyl-OH, C(O)N[$(C_1-C_4)$alkyl]$_2$, CONH$(C_1-C_6)$alkyl, C(O)$NH_2$, N[$(C_1-C_4)$alkyl]$_2$, $(C_1-C_4)$alkylene-$(C_6-C_{10})$aryl, wherein the $(C_6-C_{10})$aryl may be further substituted one to three times, preferably once, by $(C_1-C_4)$alkyl, $(C_1-C_4)$alkylene-O—$(C_1-C_6)$alkyl, $(C_6-C_{10})$aryl O—$(C_1-C_6)$alkyl-$(C_6-C_{10})$aryl, or may be vicinally substituted by a O—$(C_1-C_4)$alkylene-0 group whereby a 5-8-membered ring is formed together with the carbon atoms the oxygen atoms are attached to. More preferred substituents for $(C_6-C_{10})$aryl are halogen, CN, phenyl, O-phenyl, NH—C(O)—$(C_1-C_4)$alkyl especially NH—C(O)—$CH_3$, C(O)—$(C_1-C_4)$alkyl especially C(O)—$CH_3$, $(C_1-C_4)$alkyl especially $CH_3$ or $CF_3$, O—$(C_1-C_4)$alkyl especially O—$CH_3$, $SO_2$—$NH_2$, $SO_2$—$(C_1-C_4)$alkyl especially $SO_2$—$CH_3$ or $SO_2$—$CF_3$ or $SO_2$—N=CH—N[$(C_1-C_4)$alkyl]$_2$ especially $SO_2$—N=CH—N[$(CH_3)_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-N[$(C_1-C_4)$alkyl]$_2$, or $(C_6-C_{10})$aryl, wherein the $(C_6-C_{10})$aryl may be further substituted by $(C_1-C_4)$alkyl, O—$(C_1-C_6)$alkyl, halogen, $(C_1-C_4)$alkylene-O—$(C_1-C_6)$alkyl, O—$(C_1-C_6)$alkyl-$(C_6-C_{10})$aryl, or may be vicinally substituted by a O—$(C_1-C_4)$alkylene-0 group whereby a 5-8-membered ring is formed together with the carbon atoms the oxygen atoms are attached to. More preferred substituents for $(C_5-C_{10})$heterocyclyl groups are $(C_1-C_4)$alkyl, halogen or phenyl, wherein the phenyl may be further substituted one to three times, preferably once, by halogen, $(C_1-C_4)$alkyl or O—$(C_1-C_4)$alkyl.

The general and preferred substituents of $(C_6-C_{10})$aryl and $(C_5-C_{10})$heterocyclyl groups may be combined with the general and preferred definitions of $R_1, R_2, R_3, R_4, R_5, R_6, R_7, R_9$, n, m and L as described above.

The present invention therefore also relates to the compounds of the formula (I) and/or their pharmaceutically acceptable salts and/or their prodrugs for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formulae (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Isoquinolines and isoquinolinones can by synthesized via a variety of methods. The following general schemes illustrate some of the possible ways to access isoquinolones, but do not limit the present invention.

Scheme 1:

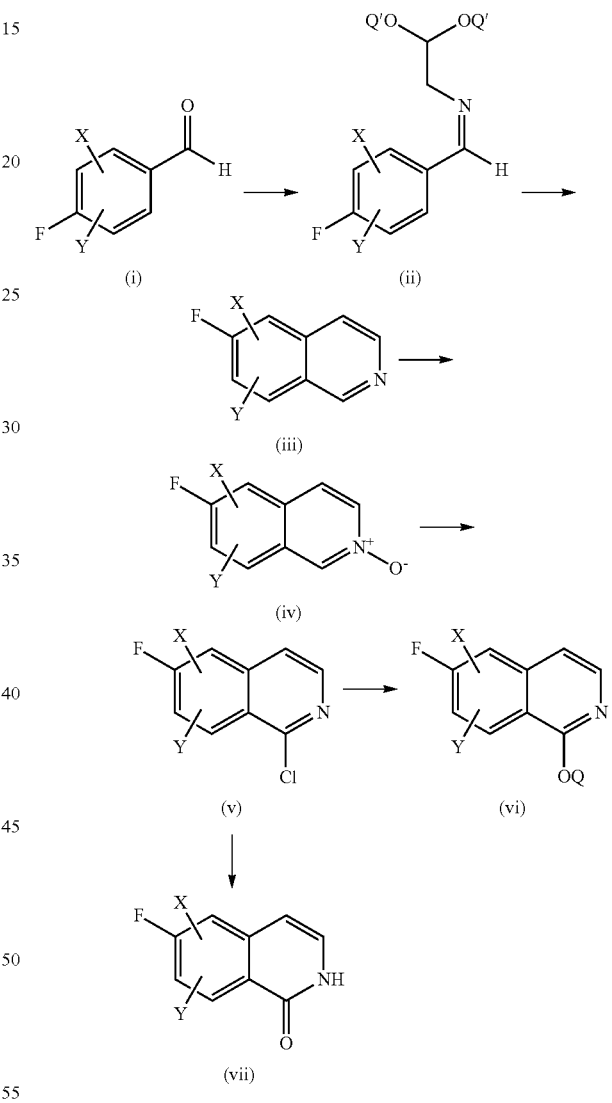

A suitably substituted aldehyde, for example substituted by X or Y being independently from each other hydrogen, alkyl, alkoxy or halide attached in a suitable position, can be reacted with a suitable compound such as for example an actual of aminoacetaldehyde for example in a solvent like THF, chloroform or toluene under acid catalysis by toluene sulfonic acid or another appropriate acid to give imine (ii) wherein Q' can be for instance methyl or ethyl, which in turn can be cyclized by different methods to the isoquinoline (iii). For example this can be done by Lewis acid catalysis by suitable Lewis acids like titanium tetrachloride, ferrous halides, aluminium halides etc. at temperatures ranging from ambient to 100° C. or by reducing the imine to the corresponding amine by action of a suitable reducing agent like sodium borohydride, converting the amine into an amide or sulphonamide by reaction with a suitable acid chloride and subsequent cyclization to the isoquinoline by action of an appropriate lewis acid. The isoquinoline (iii) itself can then be converted to the corresponding N-oxide (iv) by action of a suitable oxidative agent like hydrogen peroxide, m-chloro perbenzoic acid or others at room temperature or elevated temperature. The N-oxide (iv) can then be converted into the 1-chloro-isoquinoline derivative (v) by reacting it with a reagent like phosphorous oxy chloride in or without presence of phosphorous pentachloride. The derivative (v) can then be turned into suitable 1-alkoxy-derivatives by reacting it with various alcohols Q-OH like methanol, ethanol or benzyl alcohol in the presence of a suitable base like sodium hydride and in a suitable solvent like dimethyl formamide, dimethyl acetamide or others. Alternatively (v) can be directly converted into the isoquinolinone derivative (vii) by reacting it with a reagent like ammonium acetate.

wherein z is for example H or alkyl like methyl or ethyl, with a reagent like triethyl phosphono acetate in the presence of a suitable base like sodium hydride to give the corresponding cinnamic acid ester, which subsequently is cleaved by action of a suitable base like potassium hydroxide, sodium hydroxide or lithium hydroxide in a suitable solvent to deliver acid (ix). (ix) can then be converted in the corresponding acid chloride by well known methods, which can be transferred into the acid azide by reaction with sodium azide in a suitable solvent like ether, chloroform or acetone in or without the presence of water. The corresponding azide then can be converted into isoquinolinone (x) by reacting it in a suitable solvent like diphenylmethane or diphenylether at suitable temperature.

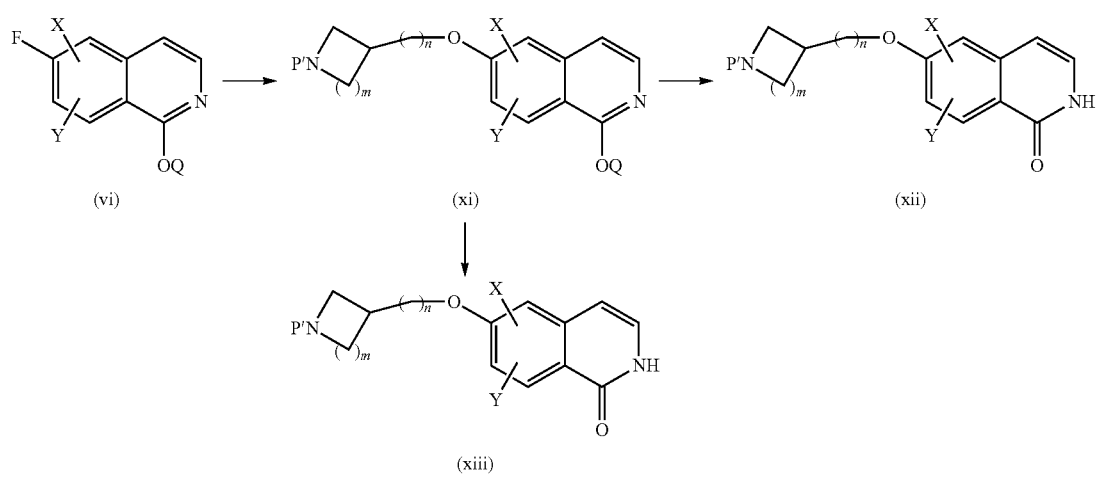

(vi)　　　　(xi)　　　　(xii)

(xiii)

The above obtained 6-Fluoro-isoquinolones, for example (vi), can be reacted with suitable P substituted amino alcohols wherein P is for example hydrogen, alkyl or a protecting group like for example Boc in the presence of base such as DBU, cesium carbonate or sodium hydride to give the corresponding alkoxy substituted derivatives (xi). Eventually, this conversion can already be performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base. Isoquinoline derivatives can be obtained by employing fluoro isoquinolines like (iii) in the reaction as described for the conversion of (vi) to (xi), in this particular case OQ equals H. the amino group of such derivatives can be modified accordingly to procedures described hereafter. The products like (xi) obtained via this method can then either be liberated or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step like for example acidic removal of Boc-groups. Furthermore an amino group can be acylated by reacting it with a suitable acid chloride in the precence of a base like triethyl amine or Hünig's base or by reacting it with a suitable carboxylic acid in the precence of a base like triethylamine of Hünig's base and a coupling reagent like EDC, PyBOP or TOTU.

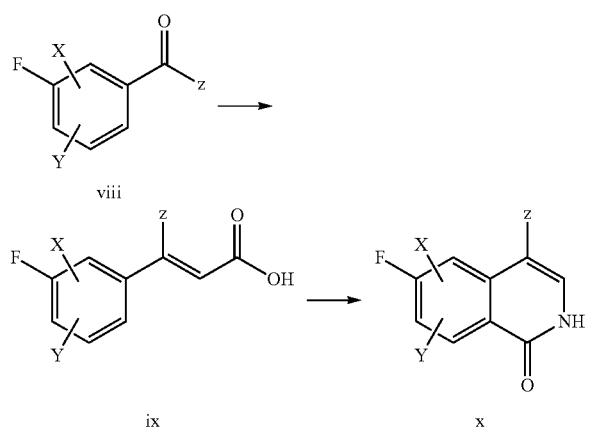

Scheme 2

Alternatively isoquinolinones can be obtained by reacting suitable 3-formylated or acylated fluorobenzenes (viii), In case of use of protected isoquinolones, cleavage of the used protection groups is required to liberate the desired isoquinolone (xii). This liberation, however, can be performed before or after the reductive amination step, depending on the nature of the used aldehyde/ketone and the protection group used.

Isoquinolone derivatives like (xii) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The general methods for the preparation of isoquinoline derivatives as described above can be readily adapted to the preparation of the compounds of the formula (I). In the following examples the preparation of the compounds of the present invention is outlined in more detail.

Accordingly, the following examples are part of and intended to illustrate but not to limit the present invention.

It is understood that modifications that do not substantially affect the activity of the various embodiments of this invention are included within the invention disclosed herein.

LC/MS-Methods:

Method A:

Stationary phase: Col YMC Jsphere 33×2

Gradient: ACN+0.05% TFA:H$_2$O+0.05% TFA 5:95 (0 min) to 95:5 (3.4 min) to 95:5 (4.4 min)

Flow 1 mL/min

Method B:

Stationary phase: Col YMC Jsphere 33×2

Gradient: ACN+0.05% TFA:H$_2$O+0.05% TFA 5:95 (0 min) to 95:5 (2.5 min) to 95:5 (3.0 min)

Flow 1 mL/min

Method C:

Stationary phase: Col YMC Jsphere ODS H80 20×2

Gradient: ACN:H$_2$O+0.05% TFA 4:96 (0 min) to 95:5 (2.0 min) to 95:5 (2.4 min)

Flow 1 mL/min

Method D:

Stationary phase: Col YMC Jsphere 33×2.1

Gradient: Grad ACN+0.08% FA:H2O+0.1% FA (Formic Acid) 5:95 (0 min) to 95:5 (2.5 min) to 95:5 (3 min)

Flow 1.3 mL/min

Method E:

Stationary phase: Col YMC Jsphere 33×2

Gradient: ACN+0.05% TFA:H$_2$O+0.05% TFA 5:95 (0 min) to 95:5 (2.5 min) to 95:5 (3.2 min)

Flow 1.3 mL/min

Method F:

Stationary phase: Col YMC-Pack Pro C18 RS 33×2.1

Gradient: Grad ACN+0.1% FA:H$_2$O+0.1% FA (Formic Acid) 5:95 (0 min) to 95:5 (2.5 min) to 95:5 (3 min)

Flow 1.3 mL/min

3-Chloro-4-fluoro-benzyl)-(2,2-dimethoxy-ethyl)-amine (1)

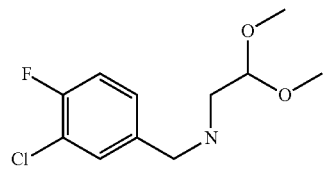 [SMILES: COC(CNCc1ccc(F)c(Cl)c1)OC]

100 g (0.63 mol) of 3-chloro-4-fluoro-benzaldehyde were dissolved in 300 ml of toluene and 66.3 g (0.63 mol) of aminoacetaldehyd-dimethylacetal were added at room temperature. After adding 12.0 g (0.06 mol) p-toluenesulfonic acid monohydrate, the reaction was heated in a Dean-Stark apparatus for 3 h. The solution was than cooled to room temperature and washed twice with saturated NaHCO$_3$-solution and water. The aqueous solutions are extracted with toluene. The combined organic layers are dried with MgSO4 and evaporated. The obtained imine-intermediate is dissolved directly in 300 mL of ethanol and 11.93 g (0.32 mol) of sodium borohydride were added in small portions. After stirring overnight, 10 mL of acetic acid were added and the solvent was removed i. vac. The residue was dissolved in dichloromethane and washed twice with water. After drying with MgSO$_4$ and evaporation of the solvent, 147.0 g of crude product were obtained as a yellow oil, which was used without further purification. R$_t$=0.81 min (Method C). Detected mass: 248.2 (M+H$^+$).

N-(3-Chloro-4-fluoro-benzyl)-N-(2,2-dimethoxy-ethyl)-4-methyl-benzene-sulfonamide (2)

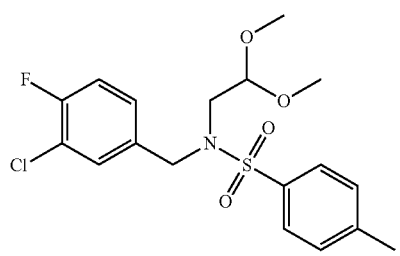 [SMILES: COC(CN(Cc1ccc(F)c(Cl)c1)S(=O)(=O)c1ccc(C)cc1)OC]

147.0 g (3-Chloro-4-fluoro-benzyl)-(2,2-dimethoxy-ethyl)-amine (1, crude product) were dissolved in 540 ml of dichloromethane/pyridine (8:1). At 0° C. a solution of 145.8 g (1.04 mol) p-toluenesulfonylchloride in 200 ml of dichloromethane was added. After 5 h at room temperature additional 20 ml of pyridine, 29.16 g (0.15 mol) p-toluene-sulfonylchloride and a catalytic amount of DMAP were added. The solution was stirred at room temperature for 7 h and then refluxed for additional 4 h. Again 29.16 g (0.15 mol) p-toluene-sulfonylchloride and a catalytic amount of DMAP were added and the mixture was stirred overnight. For workup, the solution was washed twice with 2 N HCl and twice with saturated NaHCO$_3$-solution. The organic layer was dried with MgSO$_4$ and evaporated. Final silicagel chromatography (heptane/ethyl acetate 4:1) gave 155 g of the title compound as a yellow oil. $R_f$=1.80 min (Method B). Detected mass: 370.2 (M-OMe⁻).

7-Chloro-6-fluoro-isoquinoline (3)

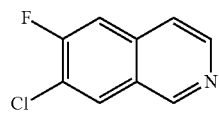 [SMILES: Fc1cc2ccncc2cc1Cl]

343.6 (2.54 mol) of AlCl₃ were suspended in 1.1 l of dichloromethane and were stirred for 30 min with a mechanical stirrer. To this suspension, a solution of 204 g (0.51 mol) (N-(3-Chloro-4-fluoro-benzyl)-N-(2,2-dimethoxy-ethyl)-4-methyl-benzene-sulfonamide (2) was added and the mixture was stirred at room temperature for 5 h. After standing overnight, the reaction suspension was poured on ice, the organic layer was separated and the aqueous phase was extracted twice with dichloromethane. The combined organic layers were washed twice with 1 N NaOH and saturated NaHCO3-solution, dried with MgSO4 and evaporated. The obtained crude product was purified by silicagel chromatography (heptane/ethyl acetate 1:1), which gave 61.3 g of the title compound. $R_f$=0.73 min (Method B). Detected mass: 182.1 (M+H⁺).

7-Chloro-6-fluoro-isoquinoline 2-oxide (4)

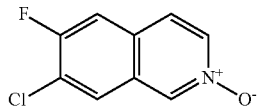 [SMILES: [O-][n+]1ccc2cc(F)c(Cl)cc2c1]

25 g (137.7 mmol) of 7-Chloro-6-fluoro-isoquinoline (3) were in dissolved in 500 ml of dichloromethane. At room temperature 50.9 g (206.5 mmol) of 3-Chloro-benzene-carboperoxoic acid (70%) were added and the mixture was stirred at room temperature until complete conversion is achieved. For workup, the precipitate was filtered off and washed with dichloromethane. The filtrate was washed twice with NaHCO₃-solution. The layers were separated and the aqueous phase was extracted twice with dichloromethane. The organic phases were dried with MgSO₄ and evaporated. The so obtained solid material (18.4 g) was used without further purification. $R_f$=0.87 min (Method C). Detected mass: 198.1/200.1 (M+H⁺).

1,7-Di-chloro-6-fluoro-isoquinoline (5)

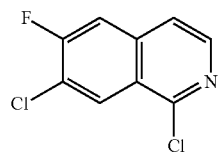 [SMILES: Fc1cc2ccnc(Cl)c2cc1Cl]

2.6 g (12.0 mmol) of 7-Chloro-6-fluoro-isoquinoline 2-oxide (4) were heated in 40 ml of POCl₃ at reflux for 4 h. After the mixture has cooled down to room temperature, it was poured on ice. The aqueous solution was extracted three times with dichloromethane. The combined organic layers were dried with MgSO₄ and evaporated to yield 2.91 g of the title compound, which was used without further purification. $R_f$=2.34 min (Method A). Detected mass: 216.0/218.0 (M+H⁺).

4-(1-Benzyloxy-7-chloro-isoquinolin-6-yloxy)-piperidine-1-carboxylic acid tert-butyl-ester (6)

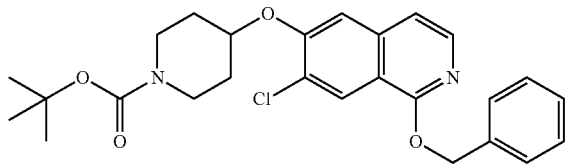 [SMILES: CC(C)(C)OC(=O)N1CCC(Oc2cc3ccnc(OCc4ccccc4)c3cc2Cl)CC1]

289.8 mg (1.44 mmol) of 4-hydroxy-piperidine-1-carboxylic acid tert-butyl-ester were dissolved in 10 ml of dimethyl acetamide and 57.6 mg (1.44 mmol) of sodium hydride (60%) were added. The reaction mixture was stirred at room temperature. After 30 minutes a solution of 310 mg (1.44 mmol) of 1,7-dichloro-6-fluoro-isoquinoline (5) in 3 ml of dimethyl acetamide was added and the mixture was stirred at room temperature for 1 h to complete conversion. Then 155.7 mg (1.44 mmol) of benzyl alcohol followed by 57.6 mg (1.44 mmol) of sodium hydride (60%) were added and stirring was continued at room temperature. To reach complete conversion, 0.5 equivalents of benzyl alcohol and sodium hydride were added twice, after 2 h and standing overnight. For working up, the solvent was evaporated, the residue was taken up in dichloromethane, washed twice with H₂O, dried with MgSO₄ and evaporated. Final purification was accomplished by preparative HPLC.

7-Chloro-6-(piperidin-4-yloxy)-2H-isoquinolin-1-one-hydrochloride (7)

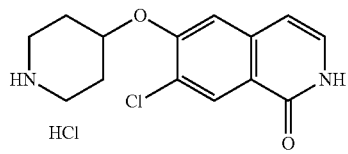 [SMILES: O=c1[nH]ccc2cc(OC3CCNCC3)c(Cl)cc12 ; Cl]

254 mg (0.52 mmol) of 4-(1-Benzyloxy-7-chloro-isoquinolin-6-yloxy)-piperidine-1-carboxylic acid tert-butyl-ester (6) were stirred in methanol/2 N HCl (1:1) at room temperature overnight. The solvent was removed i. vac. and the residue was purified by preparative HPLC. The product fractions were evaporated and dissolved in 2 N HCl. Lyophilization results in 57 mg of the desired compound. $R_f$=0.95 min (Method B). Detected mass: 279.1 (M+H⁺).

General procedure for the acylation reaction of 7-Chloro-6-(piperidin-4-yloxy)-2H-isoquinolin-1-one (7)

0.74 mmol of the carboxylic acid derivative were dissolved in 10 ml of DMF. After adding 0.74 mmol of triethylamine, 0.74 mmol of TOTU were added at 0° C. and the solution was stirred at room temperature for 30 minutes. This solution was than added to a solution of 0.74 mmol 7-chloro-6-(piperidin-4-yloxy)-2H-isoquinolin-1-one (7, free base) in 10 ml DMF at 0° C. Stirring is continued at room temperature until complete conversion is achieved. For isolation, the solvent was removed i. vac. and the residue was dissolved in dichloromethane. The solution was washed with water and dried over MgSO$_4$. The obtained crude products were purified by prep. HPLC. The product fractions were evaporated and the residues dissolved in 2 N HCl. In the case of Boc-protected product, the 2 NHCl-solutions were stirred at room temperature until complete cleavage of the Boc-group is achieved. After evaporation of the aqueous solution, the compounds were dissolved in water and freeze dried to give the desired compounds as HCl-salts.

The compounds described in the following table 1 were obtained using this general procedure.

TABLE 1

| Comp. No. | Carboxylic acid derivative | Product | R$_t$ [min] | Mass [M + H$^+$] | Method | Chemical Name |
|---|---|---|---|---|---|---|
| 8 | | | 0.87 | 350.1 | B | 7-Chloro-6-[1-(2-methylamino-acetyl)-piperidin-4-yloxy]-2H-isoquinolin-1-one |
| 9 | | | 1.47 | 466.2 | B | 2-{2-[4-(7-Chloro-1-oxo-1,2-dihydro-isoquinolin-6-yloxy)-piperidin-1-yl]-2-oxo-ethyl}-isoindole-1,3-dione |
| 10 | | | 1.08 | 392.3 | B | 6-[1-(2-Amino-3,3-dimethyl-butyryl)-piperidin-4-yloxy]-7-chloro-2H-isoquinolin-1-one |
| 11 | | | 0.90 | 350.1 | B | 6-[1-(2-Amino-propionyl)-piperidin-4-yloxy]-7-chloro-2H-isoquinolin-1-one |
| 12 | | | 0.92 | 364.2 | B | 6-[1-(2-Amino-2-methyl-propionyl)-piperidin-4-yloxy]-7-chloro-2H-isoquinolin-1-one |
| 13 | | | 0.95 | 364.2 | B | 6-[1-((S)-2-Amino-butyryl)-piperidin-4-yloxy]-7-chloro-2H-isoquinolin-1-one |
| 14 | | | 1.10 | 392.2 | B | 6-[1-((S)-2-Amino-4-methyl-pentanoyl)-piperidin-4-yloxy]-7-chloro-2H-isoquinolin-1-one |
| 15 | | | 1.00 | 376.2 | B | 7-Chloro-6-[1-((S)-pyrrolidine-2-carbonyl)-piperidin-4-yloxy]-2H-isoquinolin-1-one |
| 16 | | | 0.91 | 364.2 | B | 7-Chloro-6-[1-(2-dimethylamino-acetyl)-piperidin-4-yloxy]-2H-isoquinolin-1-one |

TABLE 1-continued

| Comp. No. | Carboxylic acid derivative | Product | $R_t$ [min] | Mass [M + H$^+$] | Method | Chemical Name |
|---|---|---|---|---|---|---|
| 17 | | | 0.98 | 350.1 | B | 6-[1-((S)-2-Amino-propionyl)-piperidin-4-yloxy]-7-chloro-2H-isoquinolin-1-one |
| 18 | | | 1.15 | 412.1 | B | 6-[1-((S)-2-Amino-2-phenyl-acetyl)-piperidin-4-yloxy]-7-chloro-2H-isoquinolin-1-one |
| 19 | | | 0.96 | 362.1 | B | 6-[1-(1-Amino-cyclopropanecarbonyl)-piperidin-4-yloxy]-7-chloro-2H-isoquinolin-1-one |
| 20 | | | 1.09 | 378.2 | B | 6-[1-((S)-2-Amino-pentanoyl)-piperidin-4-yloxy]-7-chloro-2H-isoquinolin-1-one |
| 22 | | | 1.25 | 460.1 | B | 6-{1-[(S)-2-Amino-3-(4-chloro-phenyl)-propionyl]-piperidin-4-yloxy}-7-chloro-2H-isoquinolin-1-one |
| 23 | | | 1.20 | 444.1 | B | 6-{1-[(S)-2-Amino-3-(4-fluoro-phenyl)-propionyl]-piperidin-4-yloxy}-7-chloro-2H-isoquinolin-1-one |

The following products were obtained, using 51 as isoquinolinone building block:

The compounds were obtained as HCl salts. In case of 24, cleavage of the phthalimide group was achieved in analogous manner as described for 40 (Table 2).

TABLE 2

| Compound No. | Carboxylic acid derivative | Product | $R_t$ [min] | Mass [M + H$^+$] | Method | Chemical name |
|---|---|---|---|---|---|---|
| 24 | | | 0.35 | 302.3 | B | 6-[1-(2-Amino-acetyl)-piperidin-4-yloxy]-2H-isoquinolin-1-one |

TABLE 2-continued

| Compound No. | Carboxylic acid derivative | Product | R_t [min] | Mass [M + H+] | Method | Chemical name |
|---|---|---|---|---|---|---|
| 25 | | | 1.00 | 344.2 | B | 6-[1-((R)-2-Amino-pentanoyl)-piperidin-4-yloxy]-2H-isoquinolin-1-one |
| 26 | | | 1.07 | 352.2 | B | 6-[1-((S)-2-Amino-4-methyl-pentanoyl)-piperidin-4-yloxy]-2H-isoquinolin-1-one |
| 27 | | | 1.19 | 426.2 | B | 6-{1-[(S)-2-Amino-3-(4-chloro-phenyl)-propionyl]-piperidin-4-yloxy}-2H-isoquinolin-1-one |
| 28 | | | 0.80 | 316.2 | B | 6-[1-(2-Methylamino-acetyl)-piperidin-4-yloxy]-2H-isoquinolin-1-one |
| 29 | | | 0.88 | 342.2 | B | 6-[1-((S)-Pyrrolidine-2-carbonyl)-piperidin-4-yloxy]-2H-isoquinolin-1-one |
| 30 | | | 1.06 | 358.2 | B | 6-[1-((S)-2-Amino-3,3-dimethyl-butyryl)-piperidin-4-yloxy]-2H-isoquinolin-1-one |
| 31 | | | 0.90 | 330.2 | B | 6-[1-((S)-2-Amino-butyryl)-piperidin-4-yloxy]-2H-isoquinolin-1-one |
| 32 | | | 0.92 | 316.2 | B | 6-[1-((S)-2-Amino-propionyl)-piperidin-4-yloxy]-2H-isoquinolin-1-one |

TABLE 2-continued

| Compound No. | Carboxylic acid derivative | Product | $R_t$ [min] | Mass [M + H⁺] | Method | Chemical name |
|---|---|---|---|---|---|---|
| 33 | | | 1.38 | 432.2 | B | 2-{2-Oxo-2-[4-(1-oxo-1,2-dihydro-isoquinolin-6-yloxy)-piperidin-1-yl]-ethyl}-isoindole-1,3-dione |
| 34 | | | 0.82 | 316.2 | B | 6-[1-((R)-2-Amino-propionyl)-piperidin-4-yloxy]-2H-isoquinolin-1-one |
| 35 | | | 1.02 | 378.2 | B | 6-[1-((S)-2-Amino-2-phenyl-acetyl)-piperidin-4-yloxy]-2H-isoquinolin-1-one |
| 36 | | | 1.07 | 358.2 | B | 6-[1-((S)-2-Amino-hexanoyl)-piperidin-4-yloxy]-2H-isoquinolin-1-one |
| 37 | | | 1.07 | 358.2 | B | 6-[1-((S)-2-Amino-4-methyl-pentanoyl)-piperidin-4-yloxy]-2H-isoquinolin-1-one |
| 38 | | | 1.11 | 410.2 | B | 6-{1-[(S)-2-Amino-3-(4-fluoro-phenyl)-propionyl]-piperidin-4-yloxy}-2H-isoquinolin-1-one |
| 39 | | | 0.95 | 330.2 | B | 6-[1-(2-Amino-2-methyl-propionyl)-piperidin-4-yloxy]-2H-isoquinolin-1-one |

6-[1-(2-Amino-acetyl)-piperidin-4-yloxy]-7-chloro-2H-isoquinolin-1-one (40)

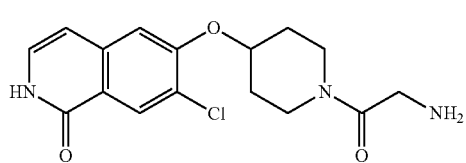 [SMILES: NCC(=O)N1CCC(Oc2cc3cc[nH]c(=O)c3cc2Cl)CC1]

140 mg (0.35 mmol) of 2-{2-[4-(7-Chloro-1-oxo-1,2-dihydro-isoquinolin-6-yloxy)-piperidin-1-yl]-2-oxo-ethyl}-isoindole-1,3-dione (9) were dissolved in 5 mL of ethanol and 30.1 mg (0.60 mmol) of hydrazine hydrate were added at room temperature. After 2 h at room temperature another 30.1 mg (0.60 mmol) of hydrazine hydrate were added and the reaction mixture was heated to 80° C. After 16 h, the solvent was evaporated i. vac. and the crude product was purified by preparative HPLC. Evaporation of the product fractions gave the desired compound as trifluoroacetate, which was dissolved in 2 N HCl. The solvent was evaporated i. vac., the residue was dissolved in H₂O. After lyophilisation, the title compound was isolated as HCl-salt. $R_t$=0.91 min (Method B). Detected mass: 336.1 (M+H⁺).

[4-(7-Chloro-1-oxo-1,2-dihydro-isoquinolin-6-yloxy)-piperidin-1-yl]-acetic acid ethyl ester (41)

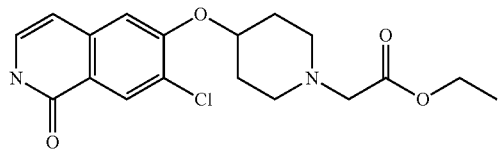 [SMILES: CCOC(=O)CN1CCC(Oc2cc3cc[nH]c(=O)c3cc2Cl)CC1]

1.5 g (5.38 mmol) of 7-Chloro-6-(piperidin-4-yloxy)-2H-isoquinolin-1-one (7, free base) were dissolved in 100 mL of methanol. At room temperature, 1.09 g (10.8 mmol) of triethylamine, 3.23 g (53.8 mmol) of acetic acid, 7.63 g (33.6 mmol) of glyoxylic acid ethyl ester and molecular sieves (4 A) were added, followed by 253.6 mg (4.04 mmol) of sodium cyanoborohydride. After stirring for 2 h at room temperature, the reaction mixture was filtered and the filtrate was evaporated i. vac. The residue was dissolved in dichloromethane and washed with 1 N NaOH and sat. NaCl-solution. The organic layer was dried with MgSO$_4$ and evaporated. The obtained crude product was used without further purification.

[4-(7-Chloro-1-oxo-1,2-dihydro-isoquinolin-6-yloxy)-piperidin-1-yl]-acetic acid (42)

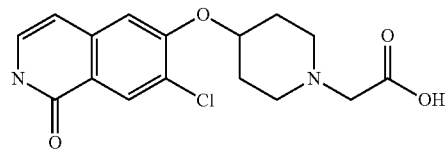 [SMILES: O=C(O)CN1CCC(Oc2cc3cc[nH]c(=O)c3cc2Cl)CC1]

1.56 g (4.27 mmol) [4-(7-Chloro-1-oxo-1,2-dihydro-isoquinolin-6-yloxy)-piperidin-1-yl]-acetic acid ethyl ester (41) were dissolved in 20 mL of methanol and 20 ml of 2N NaOH were added. After stirring for 1 h at room temperature, the solvent was removed i. vac. and the residue was dissolved in water. The aqueous solution was neutralized by adding 2 N HCl. Filtration of the precipitate and drying gave 856 mg of the title compound. R$_t$=0.82 min (Method B). Detected mass: 337.1 (M+H$^+$).

2-[4-(7-Chloro-1-oxo-1,2-dihydro-isoquinolin-6-yloxy)-piperidin-1-yl]-N,N-dimethyl-acetamide (43)

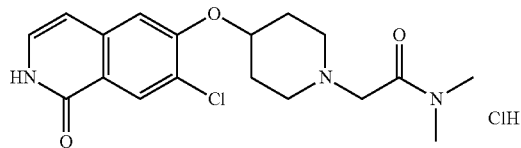 [SMILES: CN(C)C(=O)CN1CCC(Oc2cc3cc[nH]c(=O)c3cc2Cl)CC1 ; Cl]

The title compound was synthesized following the method described for 2-[4-(7-Chloro-1-oxo-1,2-dihydro-isoquinolin-6-yloxy)-piperidin-1-yl]-acetamide (42), using a 40% aqueous solution of dimethylamine. After final purification by preparative HPLC, the trifluoroacetate was obtained, which was dissolved in 2 N HCl. Evaporation of the solvent and lyophilisation of an aqueous solution of the residue gave the title compound as HCl-salt. R$_t$=0.80 min (Method B). Detected mass: 364.1 (M+H$^+$).

2-[4-(7-Chloro-1-oxo-1,2-dihydro-isoquinolin-6-yloxy)-piperidin-1-yl]-N-ethyl-acetamide (44)

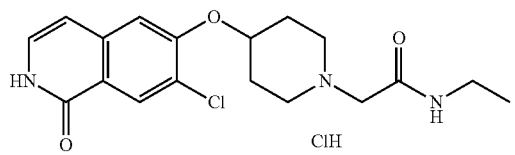 [SMILES: CCNC(=O)CN1CCC(Oc2cc3cc[nH]c(=O)c3cc2Cl)CC1 ; Cl]

The title compound was synthesized following the method described for 2-[4-(7-Chloro-1-oxo-1,2-dihydro-isoquinolin-6-yloxy)-piperidin-1-yl]-acetamide (43), using a 70% aqueous solution of ethylamine. After final purification by preparative HPLC, the trifluoroacetate was obtained, which was dissolved in 2 N HCl. Evaporation of the solvent and lyophilisation of an aqueous solution of the residue gave the title compound as HCl-salt. R$_t$=0.80 min (Method C). Detected mass: 364.2 (M+H$^+$).

2-[4-(7-Chloro-1-oxo-1,2-dihydro-isoquinolin-6-yloxy)-piperidin-1-yl]-N-methyl-acetamide (45)

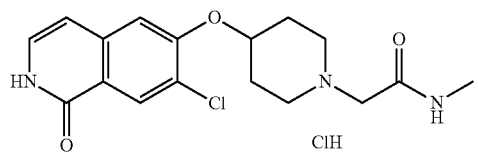 [SMILES: CNC(=O)CN1CCC(Oc2cc3cc[nH]c(=O)c3cc2Cl)CC1 ; Cl]

The title compound was synthesized following the method described for 2-[4-(7-Chloro-1-oxo-1,2-dihydro-isoquinolin-6-yloxy)-piperidin-1-yl]-acetamide (43), using a 40% aqueous solution of Methylamine. After final purification by preparative HPLC, the trifluoroacetate was obtained, which was dissolved in 2 N HCl. Evaporation of the solvent and lyophilisation of an aqueous solution of the residue gave the title compound as HCl-salt. R$_t$=0.77 min (Method C). Detected mass: 350.2 (M+H$^+$).

2-[4-(7-Chloro-1-oxo-1,2-dihydro-isoquinolin-6-yloxy)-piperidin-1-yl]-N-propyl-acetamide (46)

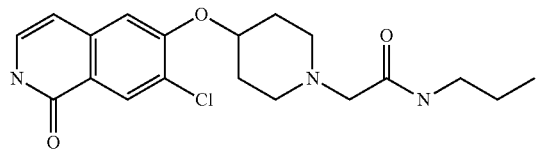
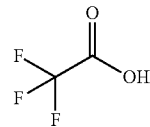

The title compound was synthesized following the method described for 2-[4-(7-Chloro-1-oxo-1,2-dihydro-isoquinolin-6-yloxy)-piperidin-1-yl]-acetamide (43), using propylamine. $R_t$=0.98 min (Method B). Detected mass: 378.2 (M+H$^+$).

6-Fluoro-isoquinolinone (47)

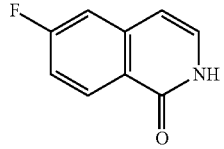 [SMILES: O=c1[nH]ccc2cc(F)ccc12]

4.8 mL (90.3 mmol, 1.5 eq.) of thionyl chloride was added portionwise to a solution of 10 g (60.2 mmol) of 3-fluoro cinnamic acid in 44 mL of chloroform and 1 mL of DMF. The reaction was heated to reflux for 2.5 h. Then the solvents were distilled to to yield 11.4 g of the crude acid chloride, which was used without any further purification.

The acid chloride was dissolved in 45 mL of acetone. At 0° C. 8.03 g of NaN$_3$ (123.5 mmol, 2 eq.) were added portionwise. Then 41 mL of water were added while the temperature was kept below 5° C. The reaction was stirred for another 1.5 h. Then 55 mL of chloroform were added. The mixture was extracted with 80 mL of water followed by 40 mL of brine. After drying over Na$_2$SO$_4$ and filtration 14 mL of diphenyl ether were added and most of the chloroform was removed in vacuo (without heating). A total removal of the chloroform should be avoided.

The solution containing the azide, diphenyl ether and the remaining chloroform was added dropwise at 260° C. within 15 minutes to a solution of 10 mL of tributyl amine in 97 mL of diphenyl ether. A vigorous reaction can be observed during the addition. The reaction was stirred for another 20 minutes at 260° C. After cooling to room temperature 270 mL of n-heptane were added. The precipitated product was filtered off and washed with ether to yield 5.65 g of the title compound. MS (DCI) Detected mass: 164.0 (M+H$^+$).

6-Fluoro-2-(4-methoxy-benzyl)-2H-isoquinolin-1-one (48)

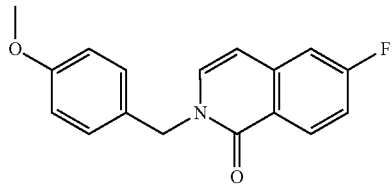 [SMILES: COc1ccc(Cn2ccc3cc(F)ccc3c2=O)cc1]

169 μL of p-methoxybenzylchloride (1.24 mmol, 1.1 eq) were added to a suspension of 200 mg of 6-fluoro-isoquinolinone (13) (1.13 mmol) and 368 mg of Cs$_2$CO$_3$ (1.36 mmol, 1.2 eq) in 3 mL of DMF. The mixture was stirred for 2 h and then poured on ice. The precipitate was filtered, washed with water and dried to yield 300 mg of the title compound. LCMS Method B, retention time 1.76 min, detected mass 284.14 [M+H]$^+$ 4,7-Dimethyl-6-Fluoro-2-(4-methoxy-benzyl)-2H-isoquinolin-1-one (49)

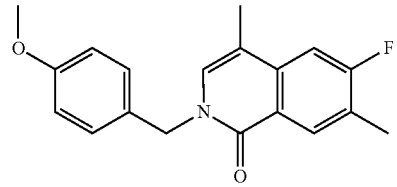 [SMILES: COc1ccc(Cn2cc(C)c3cc(F)c(C)cc3c2=O)cc1]

4,7-Dimethyl-6-Fluoro-2-(4-methoxy-benzyl)-2H-isoquinolin-1-one (49) was obtained in a similar fashion as described for (48), starting from 3-(3-Fluoro-4-methyl phenyl)-but-2-enoic acid. $R_t$=1.96 min (Method B). Detected mass: 312.1 (M+H$^+$).

5,6-Difluoro-2-(4-methoxy-benzyl)-4-methyl-2H-isoquinolin-1-one (50)

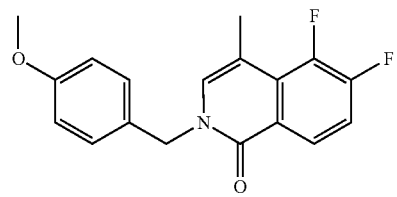 [SMILES: COc1ccc(Cn2cc(C)c3c(F)c(F)ccc3c2=O)cc1]

5,6-Difluoro-2-(4-methoxy-benzyl)-4-methyl-2H-isoquinolin-1-one (50) was obtained in a similar fashion as described for (48), starting from 3-(2,3-Difluorophenyl)-but-2-enoic acid. $R_t$=1.94 min (Method B). Detected mass: 316.1 (M+H$^+$).

6-(Piperidin-4-yloxy)-2H-isoquinolin-1-one (51)

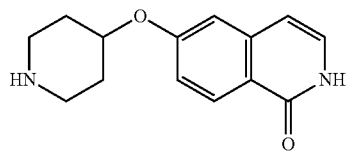

117 mg (0.58 mmol) of 4-hydroxy-piperidine-1-carboxylic acid-tert-butylester were dissolved in 2 mL of N,N-dimethyl acetamide. Under an argon atmosphere, 63.6 mg (2.7 mmol) of sodium hydride were added and the mixture was stirred at room temperature. After 30 minutes, 150 mg (0.53 mmol) of 6-fluoro-2-(4-methoxybenzyl)-2H-isoquinolin-1-one (48) were added and the solution was heated to 80° C. for 1 h. The mixture was poured in water and extracted with chloroform. The combined organic layers were dried over Na$_2$SO$_4$, filtered and evaporated. The crude intermediate was purified by preparative HPLC. The protecting groups were removed by dissolving the protected intermediate in 2 mL of TFA and heating the reaction to 150° C. for 2 h in a microwave reactor. The reaction mixture was quenched with methanol and evaporated to dryness. The remaining residue was taken up in dichloromethane, extracted three times with 1N HCl and the combined aqueous layer was extracted once with dichloromethane. The combined aqueous layer was lyophilized, the remainder was taken up in water twice and lyophilized again to give the product as HCl salt. The purity of the obtained product is sufficient, but eventually occurring impurities could be removed by silica gel chromatography or HPLC. $R_t$=0.75 min (Method B). Detected mass: 245.1 (M+H$^+$).

The following compounds were prepared in a similar fashion, using the designated starting materials, they were obtained as their HCl salts.

TABLE 3

| Compound No. | iso-quinolinone | Alcohol | Product | $R_t$ [min] | Mass [M + H$^+$] | Mtd. | Chemical name |
|---|---|---|---|---|---|---|---|
| 52 | 51 | | | 0.82 | 259.1 | B | 6-(Azepan-4-yloxy)-2H-isoquinolin-1-one |
| 53 | 51 | | | 0.54 | 231.2 | B | 6-((R)-(Pyrrolidin-3-yloxy)-2H-isoquinolin-1-one |
| 54 | 51 | | | 0.58 | 231.2 | B | 6-((S)-Pyrrolidin-3-yloxy)-2H-isoquinolin-1-one |
| 55 | 7 | | | 1.00 | 293.1 | B | 6-(Azepan-4-yloxy)-7-chloro-2H-isoquinolin-1-one |
| 56 | 7 | | | 0.71 | 265.1 | B | 6-((R)-Pyrrolidin-3-yloxy)-7-chloro-2H-isoquinolin-1-one |
| 57 | 7 | | | 0.76 | 265.1 | B | 6-((S)-Pyrrolidin-3-yloxy)-7-chloro-2H-isoquinolin-1-one |
| 58 | 7 | | | 0.67 | 251.1 | B | 6-(Azetidin-3-yloxy)-7-chloro-2H-isoquinolin-1-one |
| 59 | 49 | | | 0.83 | 287.2 | A | 6-(Azepan-4-yloxy)-4,7-dimethyl-2H-isoquinolin-1-one |
| 60 | 49 | | | 0.72 | 259.2 | A | 4,7-Dimethyl-6-((R)-pyrrolidin-3-yloxy)-2H-isoquinolin-1-one |
| 61 | 49 | | | 0.74 | 259.2 | A | 4,7-Dimethyl-6-((S)-pyrrolidin-3-yloxy)-2H-isoquinolin-1-one |

TABLE 3-continued

| Compound No. | iso-quinolinone | Alcohol | Product | R$_t$ [min] | Mass [M + H$^+$] | Mtd. | Chemical name |
|---|---|---|---|---|---|---|---|
| 62 | 49 | | | 0.74 | 273.2 | A | 4,7-Dimethyl-6-(1-methyl-pyrrolidin-3-yloxy)-2H-isoquinolin-1-one |
| 63 | 51 | | | 0.75 | 245.2 | B | 6-(Piperidin-3-yloxy)-2H-isoquinolin-1-one |
| 64 | 51 | | | 0.62 | 245.1 | B | 6-(1-Methyl-pyrrolidin-3-yloxy)-2H-isoquinolin-1-one |
| 65 | 50 | | | 1.00 | 277.5 | D | 5-Fluoro-4-methyl-6-(piperidin-4-yloxy)-2H-isoquinolin-1-one |

6-((R)-1-Benzyl-pyrrolidin-3-yloxy)-7-chloro-2H-isoquinolin-1-one (66)

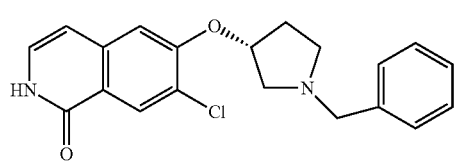 [SMILES: O=c1[nH]ccc2cc(O[C@@H]3CCN(Cc4ccccc4)C3)c(Cl)cc12]

104 mg of 60 were suspended in 2 mL of dry dichloromethane. 71 µL of triethylamine, 105 µL of benzaldehyde, 26 µL of acetic acid and 150 mg of powdered molecular sieves were added. The solution was stirred for 2 h and 220 mg of sodium triacetoxy borohydride were added. The solution was stirred for 3 h. The reaction mixture is poured in 1 N NaOH, the aqueous layer was extracted with dichloromethane:isopropanol 3:1 and the organic layer was dried over sodium sulphate and evaporated to dryness. The obtained material was purified by silica gel chromatography. R$_t$=1.14 min (Method B). Detected mass: 355.1 (M+H$^+$).

6-((S)-1-Benzyl-pyrrolidin-3-yloxy)-7-chloro-2H-isoquinolin-1-one (67)

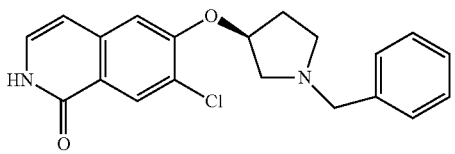 [SMILES: O=c1[nH]ccc2cc(O[C@H]3CCN(Cc4ccccc4)C3)c(Cl)cc12]

6-((S)-1-Benzyl-pyrrolidin-3-yloxy)-7-chloro-2H-isoquinolin-1-one (67) was obtained in an analogous fashion as described for (66). R$_t$=1.11 min (Method B). Detected mass: 355.1 (M+H$^+$).

6-(Azepan-4-yloxy)-7-methyl-2H-isoquinolin-1-one (68)

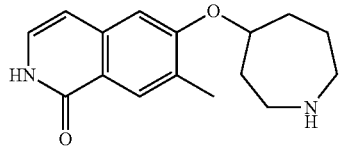 [SMILES: Cc1cc2c(=O)[nH]ccc2cc1OC1CCCNCC1]

a) 6-Fluoro-7-methyl-2H-isoquinolin-1-one

To a solution of 10.0 g (55.5 mmol) of 3-fluoro-4-methylcinnamic acid in 80 ml acetone were subsequently added at 0° C. 6.74 g (66.6 mmol) triethylamine in 10 ml acetone followed by 7.83 g (72.2 mmol) ethyl chloroformate. After stirring for 2 h at 0 to 5° C. a solution of 4.0 g (61.1 mmol) sodium azide in 9.5 ml water was added. After stirring for 1 additional h the reaction mixture was poured onto 200 ml ice water and extracted twice with chloroform. The organic phase was dried over magnesium sulfate, 40 ml diphenylether were added and the chloroform was cautiously removed in vacuo. The residue was then added dropwise into 50 ml of diphenylether which had been preheated to 245° C. After complete addition it was stirred for 1 further h at 230-250° C. After cooling down to 150° C. the reaction mixture was poured into 270 ml heptane and after further cooling in an ice bath the precipitated product was filtered by suction and 4.1 g 6-fluoro-7-methyl-2H-isoquinolin-1-one were obtained.

b) 6-Fluoro-2-(4-methoxy-benzyl)-7-methyl-2H-isoquinolin-1-one

To a solution of 9.17 g (51.8 mmol) of 6-fluoro-7-methyl-2H-isoquinolin-1-one in 80 ml DMF were added 20.2 g (62.1 mmol) caesium carbonate and then 8.92 g (56.9 mmol) 4-methoxybenzylchloride. After stirring at room temperature for 90 minutes the reaction mixture was poured into 600 ml water, stirred for 1 h, and then the precipitated product was filtrated by suction. From the mother liquor additional producted was isolated by chromatography with heptane/ethyl acetate (80:20). The combined products were recrystallized from ethyl acetate and 8.39 g 6-fluoro-2-(4-methoxy-benzyl)-7-methyl-2H-isoquinolin-1-one were received.

c) 6-(Azepan-4-yloxy)-2-(4-methoxy-benzyl)-7-methyl-2H-isoquinolin-1-one

A solution of 58 mg (0.51 mmol) azepan-4-ol in 5 ml dimethylacetamide was stirred with 45 mg (1.52 mmol) 80 percent sodium hydride for 45 minutes at room temperature. Then 150 mg (0.51 mmol) 6-fluoro-2-(4-methoxy-benzyl)-7-methyl-2H-isoquinolin-1-one in dimethylacetamide was added. The reaction mixture was heated to 80° C. for 3 days during which additional amounts of azepan-4-ol and sodium hydride were added until complete conversion of the 6-fluoro-2-(4-methoxy-benzyl)-7-methyl-2H-isoquinolin-1-one was obtained. The reaction mixture was slowly added to 10 ml water and after 1 h of stirring the product was isolated by filtration and dried overnight in vacuum. 82 mg of 6-(azepan-4-yloxy)-2-(4-methoxy-benzyl)-7-methyl-2H-isoquinolin-1-one were obtained.

d) 6-(Azepan-4-yloxy)-7-methyl-2H-isoquinolin-1-one hydrochloride 81 mg of 6-(azepan-4-yloxy)-2-(4-methoxy-benzyl)-7-methyl-2H-isoquinolin-1-one were dissolved in 0.47 trifluoroacetic acid and heated for 2 h in a microwave oven at 150° C. Then the excess trifluoroacetic acid was distilled off in vacuo and the residue was diluted with 10 ml 1 M hydrochloric acid. The aqueous phase was washed with methylene chloride twice and then freeze dried. After stirring of the residue in isopropanol and filtration 15 mg of 6-(azepan-4-yloxy)-7-methyl-2H-isoquinolin-1-one as the hydrochloride were obtained. $R_t$=0.77 min (Method C). Detected mass: 273.2 (M+H$^+$).

7-Methyl-6-((R)-1-pyrrolidin-3-ylmethoxy)-2H-isoquinolin-1-one (69)

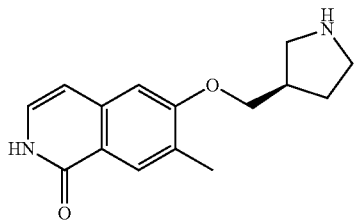 [SMILES: Cc1cc2c(=O)[nH]ccc2cc1OC[C@@H]1CCNC1]

a) (R)-3-[2-(4-Methoxy-benzyl)-7-methyl-1-oxo-1,2-dihydro-isoquinolin-6-yloxymethyl]pyrrolidine-1-carboxylic acid tert-butyl ester A solution of 271 mg (1.35 mmol) (R)-3-hydroxymethyl-pyrrolidine-1-carboxylic acid tert-butyl ester in 12 ml dimethylacetamide was stirred with 121 mg (4.0 mmol) 80 percent sodium hydride for 30 minutes at room temperature. Then a solution of 0.5 g (1.68 mmol) 6-fluoro-2-(4-methoxy-benzyl)-7-methyl-2H-isoquinolin-1-one (68, step b) in 20 ml dimethylacetamide was added. The reaction mixture was stirred at room temperature overnight, after which time the same amounts of (R)-3-hydroxymethyl-pyrrolidine-1-carboxylic acid tert-butyl ester and sodium hydride were added to drive the reaction to completion. After further 3 h stirring, the reaction mixture was slowly added to 15 ml water and after 1 h the product was isolated by filtration and dried overnight in vacuum. 0.53 g of (R)-3-[2-(4-Methoxy-benzyl)-7-methyl-1-oxo-1,2-dihydro-isoquinolin-6-yloxymethyl]-pyrrolidine-1-carboxylic acid tert-butyl ester were obtained.

b) 7-Methyl-6-((R)-1-pyrrolidin-3-ylmethoxy)-2H-isoquinolin-1-one hydrochloride 0.53 g (1.1 mmol) (R)-3-[2-(4-Methoxy-benzyl)-7-methyl-1-oxo-1,2-dihydro-isoquinolin-6-yloxymethyl]-pyrrolidine-1-carboxylic acid tert-butyl ester were dissolved in 2.5 g (22 mmol) trifluoroacetic acid. After 1 h at room temperature the mixture was heated for 2 h in a microwave oven at 150° C. Then the excess trifluoroacetic acid was distilled off in vacuo and the residue was diluted with 10 ml 1 M hydrochloric acid. The aqueous phase was washed with methylene chloride twice and then it was freeze dried to give 0.11 g 7-Methyl-6-((R)-1-pyrrolidin-3-ylmethoxy)-2H-isoquinolin-1-one as the hydrochloride. R$_f$=0.82 min (Method B). Detected mass: 259.1 (M+H$^+$).

7-Methyl-6-((S)-pyrrolidin-3-yloxy)-2H-isoquinolin-1-one (70)

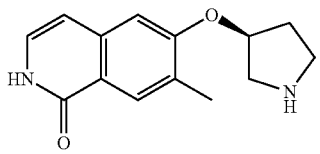 [SMILES: Cc1cc2c(=O)[nH]ccc2cc1O[C@H]1CCNC1]

a) (S)-3-[2-(4-Methoxy-benzyl)-7-methyl-1-oxo-1,2-dihydro-isoquinolin-6-yloxy]-pyrrolidine-1-carboxylic acid tert-butyl ester A solution of 252 mg (1.35 mmol) (S)-3-hydroxy-pyrrolidine-1-carboxylic acid tert-butyl ester in 12 ml dimethylacetamide was stirred with 81 mg (2.7 mmol) 80 percent sodium hydride for 30 minutes at room temperature. Then a solution of 0.4 g (1.3 mmol) 6-fluoro-2-(4-methoxy-benzyl)-7-methyl-2H-isoquinolin-1-one (68, step b) in 15 ml dimethylacetamide was added. The reaction mixture was heated to 80° C. for 2 h during which time a clear solution was obtained. The reaction mixture was slowly added to 10 ml water and after 30 minutes of stirring the product was isolated by filtration and dried overnight in vacuum. 0.54 g of (S)-3-[2-(4-Methoxy-benzyl)-7-methyl-1-oxo-1,2-dihydro-isoquinolin-6-yloxy]-pyrrolidine-1-carboxylic acid tert-butyl ester were obtained.

b) 7-Methyl-6-((S)-pyrrolidin-3-yloxy)-2H-isoquinolin-1-one hydrochloride 0.54 g (1.2 mmol) (S)-3-[2-(4-Methoxy-benzyl)-7-methyl-1-oxo-1,2-dihydro-isoquinolin-6-yloxy]-pyrrolidine-1-carboxylic acid tert-butyl ester were dissolved in 2.7 g (23 mmol) trifluoroacetic acid. After 1 h at room temperature the mixture was heated for 2 h in a microwave oven at 150° C. Then the excess trifluoroacetic acid was distilled off in vacuo and the residue was diluted with 10 ml 1 M hydrochloric acid. The aqueous phase was washed with methylene chloride twice and then it was freeze dried to give 0.256 g 7-Methyl-6-((S)-pyrrolidin-3-yloxy)-2H-isoquinolin-1-one as the hydrochloride. R$_f$=0.90 min (Method B). Detected mass: 245.2 (M+H$^+$).

7-Methyl-6-((R)-pyrrolidin-3-yloxy)-2H-isoquinolin-1-one (71)

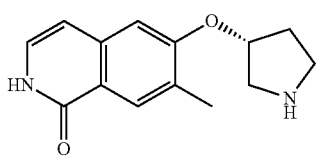 [SMILES: Cc1cc2c(=O)[nH]ccc2cc1O[C@@H]1CCNC1]

a) 2-(4-Methoxy-benzyl)-7-methyl-6-((R)-pyrrolidin-3-yloxy)-2H-isoquinolin-1-one hydrochloride A solution of 125 mg (1.0 mmol) (R)-3-pyrrolidinol hydrochloride in 9 ml dimethylacetamide was stirred with 61 mg (2.0 mmol) 80 percent sodium hydride for 30 minutes at room temperature. Then a solution of 0.3 g (1.0 mmol) 6-fluoro-2-(4-methoxy-benzyl)-7-methyl-2H-isoquinolin-1-one (68, step b) in 10 ml dimethylacetamide was added. The reaction mixture was stirred at 80° C. for 12 h, after which time the same amounts of (R)-3-pyrrolidinol hydrochloride and sodium hydride were added to drive the reaction to completion. After further 2 days heating to 80° C., the reaction mixture was slowly added to 8 ml water and extracted with methylenechloride. After evaporation the residue was dissolved in 20 ml of 1 M hydrochloric acid and washed with ethyl acetate. The aqueous phase was lyophylisized to give 247 mg of 2-(4-Methoxy-benzyl)-7-methyl-6-((R)-pyrrolidin-3-yloxy)-2H-isoquinolin-1-one hydrochloride.

b) 7-Methyl-6-((R)-pyrrolidin-3-yloxy)-2H-isoquinolin-1-one hydrochloride 245 mg of 2-(4-Methoxy-benzyl)-7-methyl-6-((R)-pyrrolidin-3-yloxy)-2H-isoquinolin-1-one hydrochloride were dissolved in 1.4 g trifluoroacetic acid and the mixture was heated for 2 h in a microwave oven at 150° C. Then the excess trifluoroacetic acid was distilled off in vacuo and the residue was diluted with 10 ml 1 M hydrochloric acid. The aqueous phase was washed with methylene chloride twice and then it was freeze dried to give 134 mg 7-Methyl-6-((R)-1-pyrrolidin-3-ylmethoxy)-2H-isoquinolin-1-one hydrochloride. R$_f$=0.92 min (Method B). Detected mass: 245.1 (M+H$^+$).

General Procedure for the Reductive Amination Reaction:

0.243 mmol of 6-(piperidin-4-yloxy)-2H-isoquinolin-1-one-hydrochloride (51) or of another suitable amine, 0.243 mmol of the aldehyde and 0.365 mmol triethylamine were stirred in 3 mL HC(OMe)$_3$ for 1 h at room temperature. The mixture was cooled to −10° C., 1.75 mL of a freshly prepared DMF solution containing 1.215 mmol NaHB(OAc)$_3$ and 1.215 mmol of HOAc were added. Stirring was continued at −10° C. for 30 min, the mixture is then allowed to warm to room temperature and left at room temperature overnight. 0.5 mL of water was added and the mixture was evaporated, dissolved in DMF and purified by preparative HPLC. The purified products were dissolved in 1 mL of HCl in isopropanol (5-6M) and stirred, until removal of Boc or isopropylidene groups is complete. 2 mL of water were added and the solution was freeze-dried to yield the hydrochlorides of the products.

The following compounds shown in the subsequent Table were synthesized in a similar fashion as described in this general procedure and obtained as hydrochloride salts (Table 4):

TABLE 4

| Compound No. | Aldehyde | Isoquinolinone | Product | [M + H]+ | R_t [min] | Method | Chemical Name |
|---|---|---|---|---|---|---|---|
| 72 | NHBoc aldehyde (S) | 63 | | 302.2 | 0.64 | B | 6-[1-((S)-2-Amino-propyl)-piperidin-3-yloxy]-2H-isoquinolin-1-one |
| 73 | NHBoc aldehyde (S) | 65 | | 334.2 | 0.80 | B | 6-[1-((S)-2-Amino-propyl)-piperidin-4-yloxy]-5-fluoro-4-methyl-2H-isoquinolin-1-one |
| 74 | oxazolidine aldehyde | 51 | | 318.3 | 0.50 | A | 6-[1-((R)-2-Amino-3-hydroxy-propyl)-piperidin-4-yloxy]-2H-isoquinolin-1-one |
| 75 | oxazolidine aldehyde | 51 | | 350.2 | 0.82 | B | 6-[1-((R)-2-Amino-3-hydroxy-propyl)-piperidin-4-yloxy]-5-fluoro-4-methyl-2H-isoquinolin-1-one |

Determination of Rho Kinase Inhibition

To measure Rho-kinase inhibition, $IC_{50}$ values were determined according to the following protocol:

Active human recombinant ROCK II (N-terminal His6-tagged recombinant human ROCK-II residues 11-552) was purchased from Upstate Ltd., Dundee, UK. The peptide substrate, Fluorescein-AKRRRLSSLRA-COOH, was obtained from JPT Peptide Technologies, Berlin, Germany. Adenosine-5′-triphosphate (ATP), bovine serum albumine (BSA), dimethylsulphoxide (DMSO), 4-(2-Hydroxyethyl)piperazine-1-ethanesulfonic acid (Hepes), Brij-35 and dithiothreitol (DTT) were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM $MgCl_2$, 2 mM DTT, 0.02% (w/v) BSA and 3% DMSO). The ROCK II enzyme was diluted to a concentration of 100 ng/ml in buffer 2 (25 mM Tris-HCl, pH 7.4, 5 mM $MgCl_2$, 2 mM DTT and 0.02% (w/v) BSA). The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015° A) (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9(5), 409-416, 2004). Separation conditions were as follows: Pressure −1.3 psi, upstream voltage −1562 V, downstream voltage −500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured.

| Example No. | pIC50 |
|---|---|
| 15 | +++++ |
| 11 | +++++ |
| 16 | +++++ |
| 19 | ++++ |
| 22 | +++++ |
| 24 | +++++ |
| 55 | +++++ |
| 46 | +++++ |
| 58 | +++++ |
| 66 | +++++ |
| 67 | ++++ |
| 68 | +++++ |
| 69 | +++++ |

-continued

| Example No. | pIC50 |
|---|---|
| 70 | +++++ |
| 75 | ++++ |

The given activity is denoted as the negative decadal logarithm of the $IC_{50}$ ($pIC_{50}$) as follows:
+: $pIC50 \leq 3.0$
++: $3.0 \leq pIC_{50} < 4.0$
+++: $4.0 \leq pIC_{50} < 5.0$
++++: $5.0 \leq pIC_{50} < 6.0$
+++++: $6.0 \leq pIC_{50}$

The invention claimed is:

1. A method for the treatment in a mammal of a disease associated with Rho-kinase and/or Rho-kinase mediated phosphorylation of myosin light chain phosphatase comprising administering to the mammal in need thereof at least one compound of the formula (I)

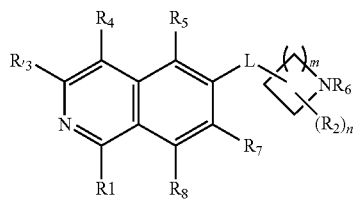

wherein
$R_1$ is OH;
$R_2$ is H, halogen or $(C_1-C_6)$alkyl;
$R_3$ is
H,
halogen,
$(C_1-C_6)$alkyl,
$(C_1-C_6)$alkylene-R',
OH,
O—R",
$NH_2$,
NHR",
NR"R" or
NH—C(O)—R",
$R_4$ is
H,
halogen,
hydroxy,
CN,
$(C_1-C_6)$alkyl,
R',
$(C_1-C_6)$alkylene-R';
$R_5$ is
H,
halogen,
CN,
$NO_2$,
$(C_1-C_6)$alkyl,
$(C_2-C_6)$alkenyl,
R',
$(C_1-C_6)$alkylene-$(C_6-C_{10})$aryl,
$(C_2-C_6)$alkenylene-$(C_6-C_{10})$aryl,
$(C_1-C_6)$alkylene-$(C_5-C_{10})$heterocyclyl,
CH(OH)—$(C_1-C_6)$alkyl,
$NH_2$,
NH—R',
NH—$SO_2H$,
NH—$SO_2$—$(C_1-C_6)$alkyl,
NH—$SO_2$—R',
NH—C(O)—$(C_1-C_6)$alkyl,
NH—C(O)—R',
C(O)N[$(C_1-C_6)$alkyl]$_2$,
C(O)OH, or
C(O)O—$(C_1-C_6)$alkyl;
$R_6$ is
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)O—$(C_1-C_6)$alkyl,
C(O)$(C_1-C_6)$alkyl,
C(O)R',
C(O)—$(C_1-C_6)$alkylene-R';
$R_7$ is
H,
Halogen,
CN,
$NO_2$,
$(C_1-C_6)$alkyl,
O—$(C_1-C_6)$alkyl,
$(C_2-C_6)$alkenyl,
R',
$(C_2-C_6)$alkenylene-$(C_6-C_{10})$aryl,
$(C_1-C_6)$alkylene-R',
CH(OH)—$(C_1-C_6)$alkyl,
$NH_2$,
NH—R',
NH—$SO_2H$,
NH—$SO_2$—$(C_1-C_6)$alkyl,
NH—$SO_2$—R',
$SO_2$—$NH_2$,
$SO_2$—NHR',
NH—C(O)—$(C_1-C_6)$alkyl,
NH—C(O)—R',
C(O)N[$(C_1-C_6)$alkyl]$_2$,
C(O)OH, or
C(O)O—$(C_1-C_6)$alkyl;
$R_8$ is H, halogen or $(C_1-C_6)$alkyl;
n is 1, 2, 3 or 4;
m is 1, 2, 3, 4 or 5; and
L is O or O—$(C_1-C_6)$alkylene;
wherein
R' is
$(C_3-C_8)$cycloalkyl,
$(C_5-C_{10})$heterocyclyl,
$(C_6-C_{10})$aryl;
R" is
$(C_3-C_8)$cycloalkyl,
$(C_5-C_{10})$heterocyclyl,
$(C_6-C_{10})$aryl,
$(C_1-C_6)$alkyl,
$(C_1-C_6)$alkylene-R',
$(C_1-C_6)$alkylene-O—$(C_1-C_6)$alkyl,
$(C_1-C_6)$alkylene-O—R', or
$(C_1-C_6)$alkylene-$NR_xR_y$; and
wherein $R_x$ and $R_y$ are independently of each other
$(C_1-C_6)$alkyl,
$(C_5-C_{10})$heterocyclyl,
$(C_6-C_{10})$aryl,
$(C_1-C_4)$alkylene-$(C_5-C_{10})$heterocyclyl,
$(C_1-C_4)$alkylene-$(C_6-C_{10})$aryl,
$(C_1-C_4)$alkylene-NH$(C_1-C_6)$alkyl,
$(C_1-C_4)$alkylene-N[$(C_1-C_6)$alkyl]$_2$,
$(C_1-C_4)$alkylene-N[$(C_6-C_{10})$aryl]$_2$, or ($C_1$-$C_4$)alkylene-N[($C_5$-$C_{10}$)heterocyclyl]$_2$;

wherein in residues $R_4$, $R_5$, $R_6$, $R_7$ and $R_8$ alkyl, alkylene or cycloalkyl can optionally be substituted one or more times by OH, OCH$_3$, COOH, COOCH$_3$, NH$_2$, NHCH$_3$, N(CH$_3$)$_2$, CONHCH$_3$ or CON(CH$_3$)$_2$;

wherein in residues $R_2$ to $R_8$ alkyl or alkylene can optionally be substituted one or more times by halogen;

wherein in residues $R_3$ to $R_8$ ($C_6$-$C_{10}$)aryl and ($C_5$-$C_{10}$) heterocyclyl are unsubstituted or substituted one or more times by suitable groups independently selected from halogen, OH, NO$_2$, N$_3$, CN, C(O)—($C_1$-$C_6$)alkyl, C(O)—($C_6$-$C_{10}$)aryl, COOH, COO($C_1$-$C_6$)alkyl, CONH$_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-NH$_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, PO$_3$H$_2$, SO$_3$H, SO$_2$—NH$_2$, SO$_2$NH($C_1$-$C_6$)alkyl, SO$_2$N[($C_1$-$C_6$)alkyl]$_2$, S—($C_1$-$C_6$)alkyl; SO—($C_1$-$C_6$)alkyl, SO$_2$—($C_1$-$C_6$)alkyl, SO$_2$—N=CH—N[($C_1$-$C_6$)alkyl]$_2$, C(NH)(NH$_2$), NH$_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—SO$_2$—($C_1$-$C_6$)alkyl, NH—SO$_2$—($C_6$-$C_{10}$)aryl, NH—SO$_2$—($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heterocyclyl, ($C_1$-$C_6$)alkylene-($C_5$-$C_{10}$)heterocyclyl, or O—($C_1$-$C_6$)alkylene-($C_5$-$C_{10}$)heterocyclyl, wherein the ($C_6$-$C_{10}$)aryl or ($C_5$-$C_{10}$)heterocyclyl may be substituted one to three times by a group independently selected from halogen, OH, NO$_2$, CN, O—($C_1$-$C_6$)alkyl, ($C_1$-$C_6$)alkyl, NH$_2$, NH($C_1$-$C_6$)alkyl, N[($C_1$-$C_6$)alkyl]$_2$, SO$_2$CH$_3$, COOH, C(O)O—($C_1$-$C_6$)alkyl, CONH$_2$, ($C_1$-$C_6$)alkylene-O—($C_1$-$C_6$)alkyl, ($C_1$-$C_6$)alkylene-O—($C_6$-$C_{10}$)aryl, or O—($C_1$-$C_6$)alkylene-($C_6$-$C_{10}$)aryl;

or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to;

and wherein aryl or heterocyclyl substituents of ($C_6$-$C_{10}$) aryl and ($C_5$-$C_{10}$)heterocyclyl groups may not be further substituted by an aryl or heterocyclyl containing group;

or their stereoisomeric and/or tautomeric forms and/or their pharmaceutically acceptable salts.

2. The method according to claim 1, wherein the disease is selected from the group consisting of hypertension, pulmonary hypertension, ocular hypertension, retinopathy, glaucoma, peripheral circulatory disorder, peripheral arterial occlusive disease (PAOD), coronary heart disease, angina pectoris, heart hypertrophy, heart failure, ischemic diseases, ischemic organ failure, thrombotic disorders, stroke, cerebral vasospasm, cerebral ischemia, Alzheimer's disease, arteriosclerosis, blood vessel restenosis, or atherosclerosis.

3. The method according to claim 1 wherein the compound of formula (I) is characterized by the formula (III)

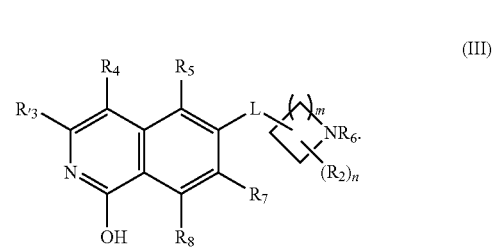

(III)

4. The method according to claim 1 wherein the compound of formula (I) is characterized by the formula (III')

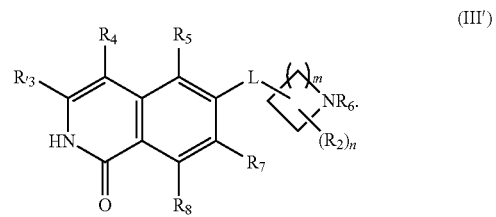

(III')

5. The method according to claim 1 wherein in formula (I) $R_3$ is H, halogen, ($C_1$-$C_4$)alkylene-R', O—R" or NHR".

6. The method according to claim 1 wherein in formula (I) $R_8$ is H, halogen or ($C_1$-$C_4$)alkyl.

7. The method according to claim 1 wherein in formula (I) $R_4$ is H, halogen or ($C_1$-$C_6$)alkyl.

8. The method according to claim 1 wherein in formula (I) $R_5$ is H, halogen, CN, ($C_1$-$C_6$)alkyl, ($C_2$-$C_6$)alkenyl, R', NH—($C_6$-$C_{10}$)aryl, ($C_1$-$C_6$)alkylene-($C_6$-$C_{10}$)aryl or ($C_1$-$C_6$)alkylene-($C_5$-$C_{10}$)heterocyclyl.

9. The method according to claim 1 wherein in formula (I) $R_7$ is H, halogen, CN, ($C_1$-$C_6$)alkyl, O—($C_1$-$C_6$)alkyl, ($C_2$-$C_6$)alkenyl, R' or ($C_1$-$C_6$)alkylene-($C_3$-$C_8$)cycloalkyl.

10. The method according to claim 1 wherein in formula (I) m is 2, 3, or 4.

11. The method according to claim 1 wherein in formula (I) m is 3.

12. The method according to claim 1 wherein in formula (I) $R_2$ is H, halogen, or ($C_1$-$C_4$)alkyl.

13. The method according to claim 1 wherein in formula (I) n is 1, 2 or 3.

14. The method according to claim 1 wherein in formula (I) $R_6$ is
($C_1$-$C_6$)alkylene-C(O)N[($C_1$-$C_6$)alkyl]$_2$,
($C_1$-$C_6$)alkylene-C(O)NH—($C_1$-$C_6$)alkyl,
($C_1$-$C_6$)alkylene-C(O)O—($C_1$-$C_6$)alkyl,
C(O)($C_1$-$C_6$)alkyl,
C(O)($C_5$-$C_{10}$)heterocyclyl,
C(O)($C_3$-$C_8$)cycloalkyl
C(O)($C_1$-$C_6$)alkylene-($C_3$-$C_8$)cycloalkyl,
C(O)($C_1$-$C_6$)alkylene-($C_5$-$C_{10}$)heterocyclyl, or
C(O)($C_1$-$C_6$)alkylene-($C_6$-$C_{10}$)aryl.

15. The method according to claim 1 wherein in formula (I) $R_6$ is
C(O)($C_1$-$C_6$)alkyl,
C(O)($C_3$-$C_8$)cycloalkyl,
C(O)—($C_5$-$C_{10}$)heterocyclyl,
C(O)($C_1$-$C_4$)alkylene-($C_5$-$C_{10}$)heterocyclyl, or
C(O)($C_1$-$C_4$)alkylene-($C_6$-$C_{10}$)aryl.

16. The method according to claim 1 wherein in formula (I) $R_6$ is
C(O)($C_1$-$C_6$)alkyl;
C(O)($C_3$-$C_6$)cycloalkyl;

C(O)—($C_5$-$C_6$)heterocyclyl wherein the heterocyclyl is unsubstituted;

C(O)($C_1$-$C_4$)alkylene-($C_5$-$C_{10}$)heterocyclyl wherein the heterocyclyl is unsubstituted; or C(O)($C_1$-$C_4$)alkylene-($C_6$-$C_{10}$)aryl wherein the aryl is unsubstituted or substituted one or more times by halogen;

and wherein a ($C_1$-$C_4$)alkyl or ($C_1$-$C_6$)alkyl residue is unsubstituted or substituted one to three times by a group independently selected from halogen, OH, $NH_2$, $NH(CH_3)$ or $N(CH_3)_2$, a ($C_1$-$C_4$)alkylene residue is unsubstituted or substituted once by amino or $N(CH_3)_2$ and a ($C_3$-$C_8$)cycloalkyl residue is unsubstituted or substituted once by $NH_2$.

17. The method according to claim 1 wherein in formula (I) m is 3 and L is attached to the 3-position or to the 4-position of the piperidine ring.

18. The method according to claim 1 wherein in formula (I) L is O-methylene, O-ethylene, or O.

19. The method according to claim 1 wherein in formula (I)
$R_1$ is OH;
$R_2$ is hydrogen, halogen, or ($C_1$-$C_6$)alkyl;
$R_3$ is H, halogen, ($C_1$-$C_4$)alkylene-R', O—R" or NHR";
$R_4$ is H, halogen or ($C_1$-$C_6$)alkyl;
$R_5$ is H, ($C_1$-$C_6$)alkyl, halogen, CN, ($C_2$-$C_6$)alkenyl, ($C_6$-$C_{10}$)aryl, NH—($C_6$-$C_{10}$)aryl, ($C_1$-$C_6$)alkylene-($C_6$-$C_{10}$)aryl, ($C_5$-$C_{10}$)heterocyclyl or ($C_1$-$C_6$)alkylene-($C_5$-$C_{10}$)heterocyclyl;
$R_6$ is, ($C_1$-$C_6$)alkylene-C(O)N[($C_1$-$C_4$)alkyl]$_2$, C(O)($C_1$-$C_6$)alkyl, C(O)($C_3$-$C_8$)cycloalkyl, C(O)—($C_1$-$C_6$)alkylene-$C_3$-$C_8$)cycloalkyl, C(O)($C_1$-$C_6$)alkylene-$C_5$-$C_{10}$)heterocyclyl, or C(O)—($C_1$-$C_6$)alkylene-($C_6$-$C_{10}$)aryl;
$R_7$ is H, halogen, CN, ($C_1$-$C_6$)alkyl, O—($C_1$-$C_6$)alkyl, ($C_2$-$C_6$)alkenyl or R';
$R_8$ is H, halogen or ($C_1$-$C_6$)alkyl;
m is 2, 3 or 4
n is 1, 2 or 3, and
L is O,O-methylene or O-ethylene.

20. The method according to claim 1 wherein in formula (I)
$R_1$ is OH;
$R_2$ is H or ($C_1$-$C_4$)alkyl;
$R_3$ is H, halogen or NHR", wherein R" is defined as above;
$R_4$ is H, halogen or ($C_1$-$C_4$)alkyl;
$R_5$ is H, ($C_1$-$C_6$)alkyl, halogen, ($C_2$-$C_4$)alkenyl, ($C_6$-$C_{10}$)aryl, ($C_1$-$C_6$)alkylene-($C_6$-$C_{10}$)aryl or ($C_5$-$C_{10}$)heterocyclyl;
$R_6$ is C(O)($C_1$-$C_6$)alkyl, C(O)($C_3$-$C_8$)cycloalkyl, C(O)—($C_5$-$C_{10}$)heterocyclyl, C(O)($C_1$-$C_6$)alkylene-($C_3$-$C_8$)cycloalkyl, C(O)($C_1$-$C_6$)alkylene-($C_5$-$C_{10}$)heterocyclyl, or C(O)($C_1$-$C_6$)alkylene-($C_6$-$C_{10}$)aryl;
$R_7$ is H, halogen, CN, ($C_1$-$C_6$)alkyl, O($C_1$-$C_6$)alkyl, ($C_2$-$C_6$)alkenyl or R';
$R_8$ is H, halogen or ($C_1$-$C_6$)alkyl;
m is 2, 3 or 4
n is 1, 2 or 3; and
L is O.

* * * * *